United States Patent
Jonas

(10) Patent No.: US 8,236,004 B2
(45) Date of Patent: *Aug. 7, 2012

(54) INSERTER FOR MINIMALLY INVASIVE JOINT SURGERY HAVING AN INTERCHANGEABLE PROSTHESIS ENGAGING PISTON

(75) Inventor: Burgi Jonas, Moutier (CH)

(73) Assignee: Greatbatch Medical S.A., Orvin (CH)

( * ) Notice: Subject to any disclaimer, the term of this patent is extended or adjusted under 35 U.S.C. 154(b) by 364 days.

This patent is subject to a terminal disclaimer.

(21) Appl. No.: 12/685,019

(22) Filed: Jan. 11, 2010

(65) Prior Publication Data

US 2010/0106159 A1    Apr. 29, 2010

Related U.S. Application Data

(62) Division of application No. 11/741,868, filed on Apr. 30, 2007, now Pat. No. 7,857,816.

(60) Provisional application No. 60/746,061, filed on May 1, 2006, provisional application No. 60/822,239, filed on Aug. 13, 2006.

(51) Int. Cl.
*A61B 17/56* (2006.01)
*A61F 2/34* (2006.01)

(52) U.S. Cl. .................. 606/91; 623/22.12

(58) Field of Classification Search .......... 606/81, 606/91, 99, 100; 623/22.12

See application file for complete search history.

(56) References Cited

U.S. PATENT DOCUMENTS

| | | | |
|---|---|---|---|
| 1,942,422 A | 6/1931 | Hanna | |
| 4,305,394 A | 12/1981 | Bertuch, Jr. | |
| D272,648 S | 2/1984 | Bolesky et al. | |
| D273,806 S | 5/1984 | Bolesky et al. | |
| 4,475,549 A | 10/1984 | Oh | |
| 4,520,511 A | 6/1985 | Gianezio et al. | |
| 4,528,980 A | 7/1985 | Kenna | |
| 4,587,964 A | 5/1986 | Walker et al. | |
| 4,632,111 A | 12/1986 | Roche | |
| 4,716,894 A | 1/1988 | Lazzeri et al. | |
| 4,765,328 A | 8/1988 | Keller et al. | |
| 4,904,267 A | 2/1990 | Bruce et al. | |

(Continued)

FOREIGN PATENT DOCUMENTS

EP    0453694    10/1991

(Continued)

OTHER PUBLICATIONS

European Search Report dated Apr. 15, 2011.

*Primary Examiner* — Thomas Barrett
*Assistant Examiner* — Michael T Schaper
(74) *Attorney, Agent, or Firm* — Michael F. Scalise

(57) ABSTRACT

An acetabular inserter (10) aids a surgeon in controlling the installation of an acetabular cup prosthesis (11) having a central, female aperture (13). The inserter includes an inserter head (20), a housing (12) and a locking mechanism. The housing (12) is attached to the inserter head, the housing enclosing a drive train (14) having, at a far end (134), a prosthesis engaging thread (124), and at the opposite end (42'), a handle (20) which facilitates turning of the drive train by the operator. The locking mechanism is associated with the housing which selectively locks the drive train, and thus the prosthesis, in position. The opposite end (42') of the drive train has a latch device which enables quick removal from the housing for cleaning and sterilization.

33 Claims, 18 Drawing Sheets

U.S. PATENT DOCUMENTS

| | | | |
|---|---|---|---|
| 4,919,679 A | 4/1990 | Averill et al. | |
| 4,921,493 A | 5/1990 | Webb, Jr. et al. | |
| 5,019,105 A | 5/1991 | Wiley | |
| 5,037,424 A | 8/1991 | Aboczsky | |
| 5,061,270 A | 10/1991 | Aboczky | |
| 5,062,854 A | 11/1991 | Noble et al. | |
| 5,089,003 A | 2/1992 | Fallin et al. | |
| 5,116,339 A | 5/1992 | Glock | |
| 5,124,106 A | 6/1992 | Morr et al. | |
| 5,133,766 A | 7/1992 | Halpern | |
| 5,169,399 A | 12/1992 | Ryland et al. | |
| 5,190,549 A | 3/1993 | Miller et al. | |
| 5,234,432 A | 8/1993 | Brown | |
| 5,261,915 A | 11/1993 | Durlacher et al. | |
| 5,324,293 A | 6/1994 | Rehmann | |
| 5,342,362 A | 8/1994 | Kenyon et al. | |
| 5,364,403 A | 11/1994 | Petersen et al. | |
| 5,417,696 A | 5/1995 | Kashuba et al. | |
| 5,443,471 A | 8/1995 | Swajger | |
| 5,454,815 A | 10/1995 | Geisser et al. | |
| 5,485,887 A | 1/1996 | Mandanis | |
| 5,540,697 A | 7/1996 | Rehmann et al. | |
| 5,584,837 A | 12/1996 | Peterson | |
| 5,658,294 A | 8/1997 | Sederholm | |
| 5,665,091 A | 9/1997 | Noble et al. | |
| 5,683,399 A | 11/1997 | Jones | |
| 5,707,374 A | 1/1998 | Schmidt | |
| 5,720,750 A | 2/1998 | Koller et al. | |
| 5,863,295 A | 1/1999 | Averill et al. | |
| 5,913,860 A | 6/1999 | Scholl | |
| 5,976,148 A | 11/1999 | Charpenet et al. | |
| 5,993,455 A | 11/1999 | Noble | |
| 6,063,124 A | 5/2000 | Amstutz | |
| 6,120,508 A | 9/2000 | Grunig et al. | |
| 6,197,065 B1 | 3/2001 | Martin et al. | |
| 6,432,141 B1 | 8/2002 | Stocks et al. | |
| 6,451,058 B2 | 9/2002 | Tuke et al. | |
| 6,626,913 B1 | 9/2003 | McKinnon et al. | |
| 6,663,636 B1 | 12/2003 | Lin | |
| 6,811,569 B1 | 11/2004 | Afriat et al. | |
| 7,090,700 B2 * | 8/2006 | Curtis | 623/38 |
| 7,192,449 B1 | 3/2007 | McQueen et al. | |
| 7,335,207 B1 | 2/2008 | Smith | |
| 7,341,593 B2 | 3/2008 | Auxepaules et al. | |
| 7,396,357 B2 | 7/2008 | Tornier et al. | |
| 7,585,301 B2 | 9/2009 | Santarella et al. | |
| 7,591,821 B2 | 9/2009 | Kelman | |
| 7,604,667 B2 | 10/2009 | DeSmet et al. | |
| 7,621,921 B2 | 11/2009 | Parker | |
| 7,922,726 B2 | 4/2011 | White | |
| 2001/0051830 A1 | 12/2001 | Tuke et al. | |
| 2002/0004660 A1 | 1/2002 | Henniges et al. | |
| 2002/0116007 A1 | 8/2002 | Lewis | |
| 2002/0177854 A1 | 11/2002 | Tuke et al. | |
| 2002/0193797 A1 | 12/2002 | Johnson et al. | |
| 2003/0009234 A1 | 1/2003 | Treacy et al. | |
| 2003/0050645 A1 | 3/2003 | Parker et al. | |
| 2003/0083668 A1 | 5/2003 | Rogers et al. | |
| 2003/0088316 A1 | 5/2003 | Ganjianpour | |
| 2003/0187512 A1 | 10/2003 | Frederick et al. | |
| 2003/0220698 A1 | 11/2003 | Mears et al. | |
| 2003/0229356 A1 | 12/2003 | Dye | |
| 2004/0073225 A1 * | 4/2004 | Subba Rao | 606/91 |
| 2004/0087951 A1 * | 5/2004 | Khalili | 606/69 |
| 2004/0215200 A1 | 10/2004 | Tornier et al. | |
| 2005/0033430 A1 * | 2/2005 | Powers et al. | 623/17.11 |
| 2005/0038443 A1 | 2/2005 | Hedley et al. | |
| 2005/0075736 A1 | 4/2005 | Collazo | |
| 2005/0137603 A1 | 6/2005 | Belew et al. | |
| 2005/0171548 A1 | 8/2005 | Kelman | |
| 2005/0187562 A1 | 8/2005 | Grimm et al. | |
| 2005/0222572 A1 | 10/2005 | Chana | |
| 2005/0228395 A1 | 10/2005 | Auxepaules et al. | |
| 2005/0234462 A1 | 10/2005 | Hershberger | |
| 2005/0246031 A1 | 11/2005 | Frederick et al. | |
| 2006/0052780 A1 | 3/2006 | Errico et al. | |
| 2006/0149285 A1 | 7/2006 | Burgi et al. | |
| 2007/0156155 A1 | 7/2007 | Parker | |
| 2007/0167952 A1 | 7/2007 | Burgi et al. | |
| 2007/0225725 A1 | 9/2007 | Heavener et al. | |
| 2007/0270783 A1 | 11/2007 | Zumsteg et al. | |
| 2007/0288096 A1 | 12/2007 | Surma | |
| 2007/0293869 A1 | 12/2007 | Conte et al. | |
| 2008/0004628 A1 | 1/2008 | White | |
| 2008/0021481 A1 | 1/2008 | Burgi | |
| 2008/0033444 A1 | 2/2008 | Bastian et al. | |
| 2008/0077249 A1 | 3/2008 | Gradel | |
| 2008/0146969 A1 | 6/2008 | Kurtz | |
| 2008/0154261 A1 | 6/2008 | Burgi | |
| 2008/0243127 A1 | 10/2008 | Lang et al. | |
| 2008/0255565 A1 | 10/2008 | Fletcher | |
| 2008/0255568 A1 | 10/2008 | Tornier et al. | |
| 2008/0262503 A1 | 10/2008 | Muller | |
| 2008/0275450 A1 | 11/2008 | Myers et al. | |
| 2009/0112214 A1 | 4/2009 | Philippon et al. | |
| 2009/0182334 A1 | 7/2009 | Brehm | |
| 2009/0192515 A1 | 7/2009 | Lechot et al. | |
| 2009/0240256 A1 | 9/2009 | Smith | |
| 2009/0281545 A1 | 11/2009 | Stubbs | |

FOREIGN PATENT DOCUMENTS

| | | |
|---|---|---|
| EP | 0470912 | 12/1992 |
| EP | 0535973 | 4/1993 |
| EP | 357302 | 7/1994 |
| EP | 638299 | 2/1995 |
| EP | 1308140 | 5/2003 |
| EP | 1190687 | 7/2004 |
| EP | 1438936 | 7/2004 |
| EP | 1447058 | 8/2004 |
| WO | 9511641 | 5/1995 |
| WO | 0012832 | 3/2000 |
| WO | 0106964 | 2/2001 |
| WO | WO0106964 | 2/2001 |
| WO | 2005044153 | 5/2005 |
| WO | 2006061708 | 6/2006 |
| WO | 2007098549 | 9/2007 |
| WO | 2008128282 | 10/2008 |
| WO | 2009136284 | 11/2009 |

* cited by examiner

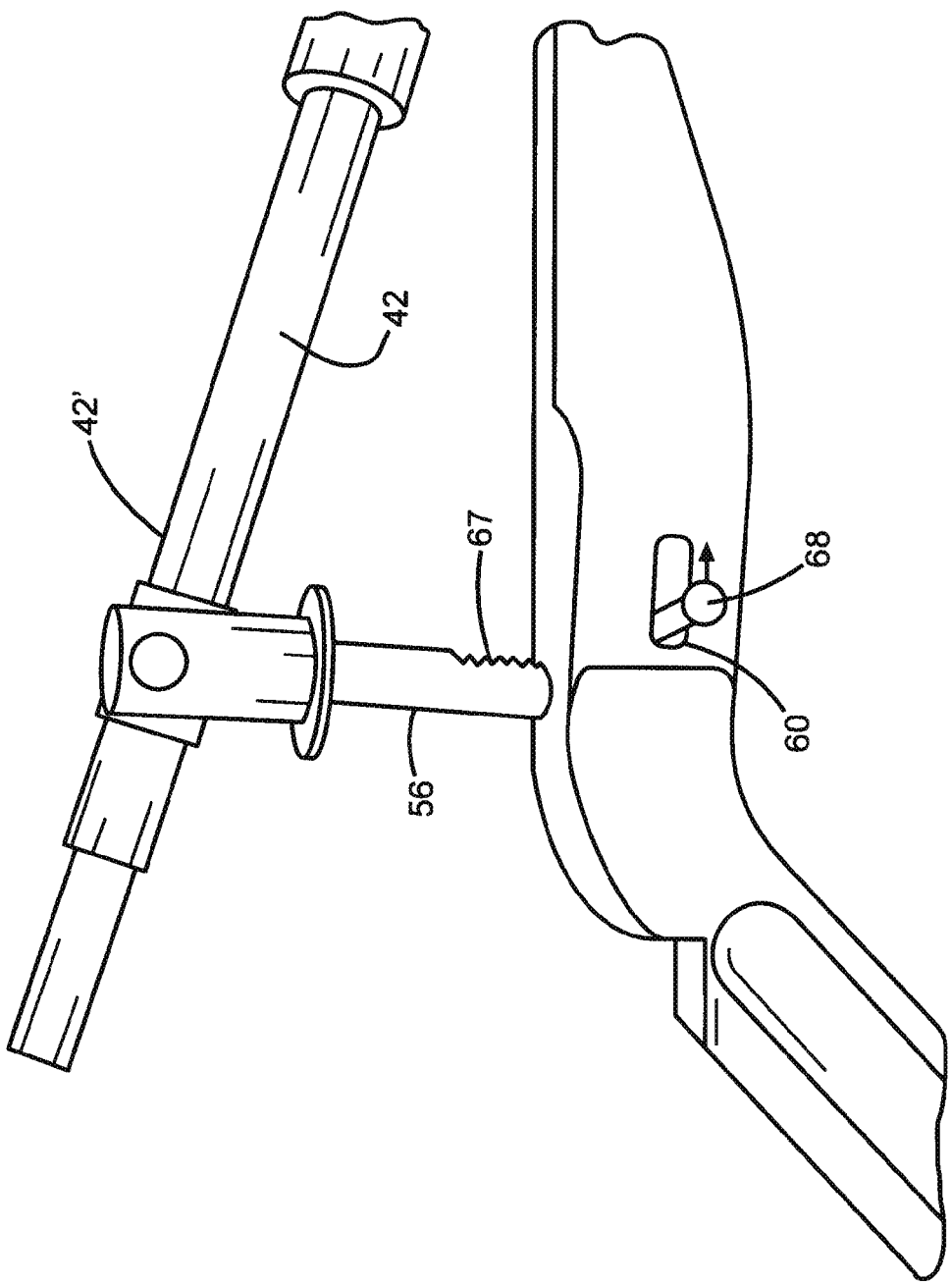

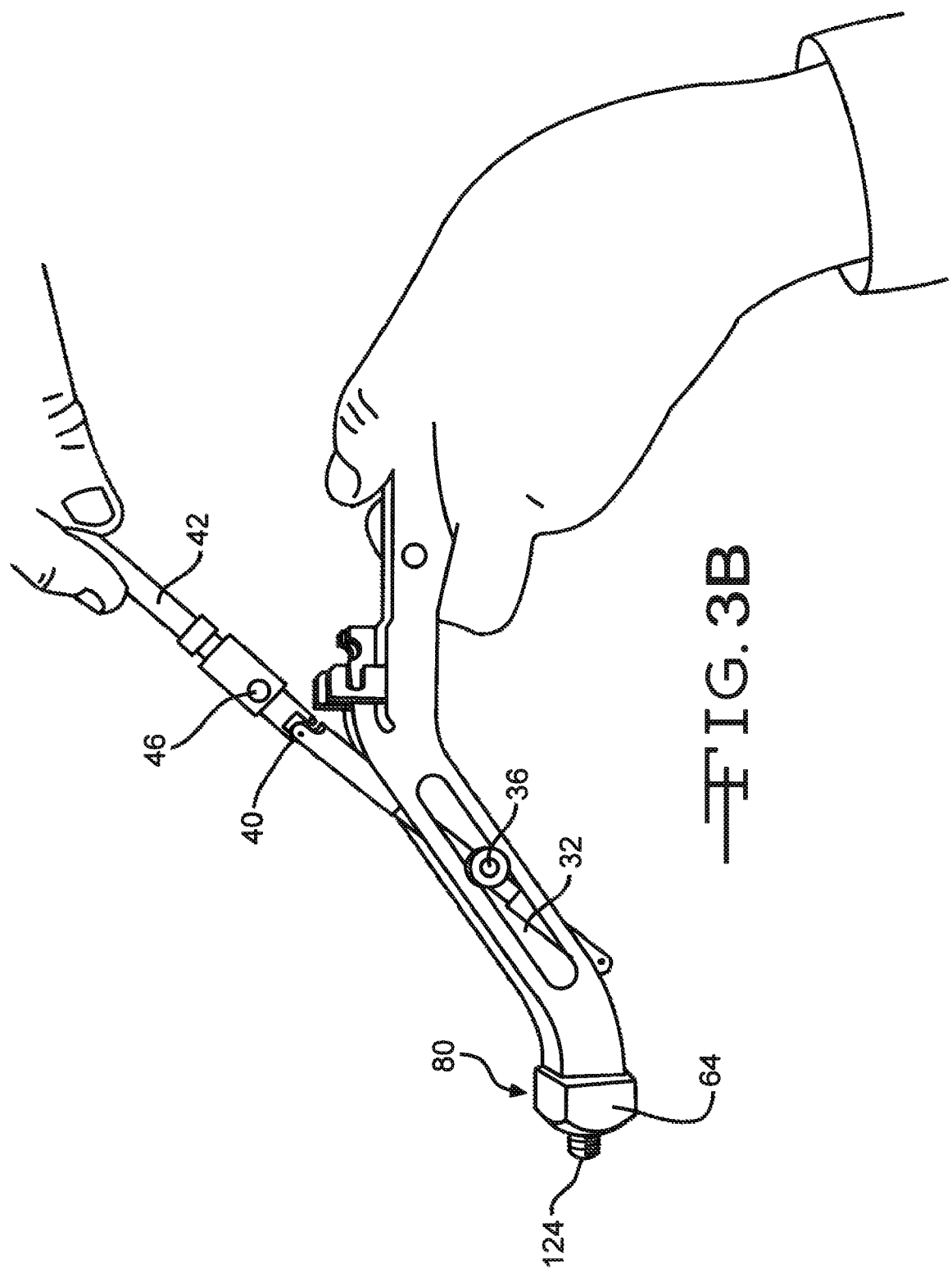

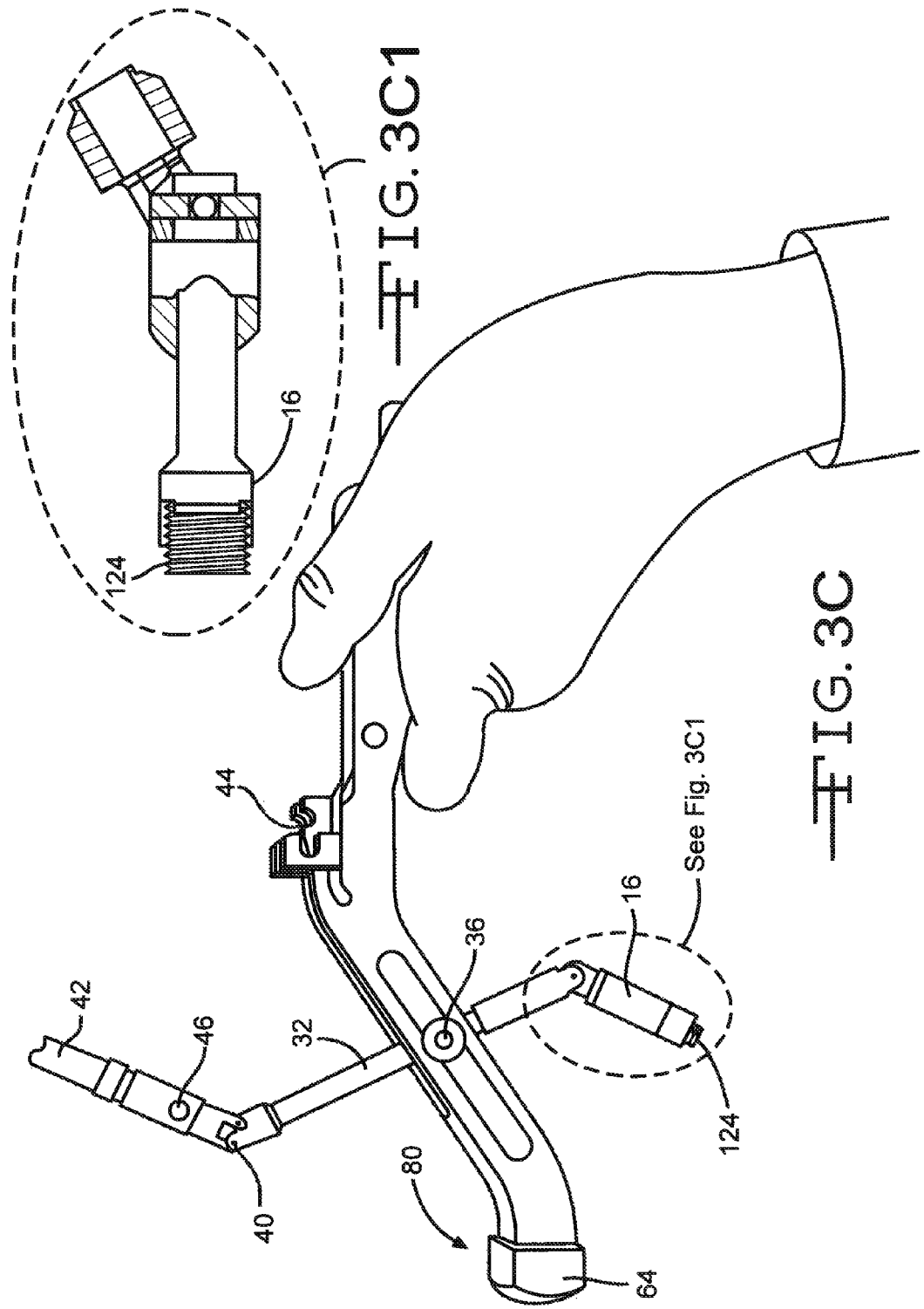

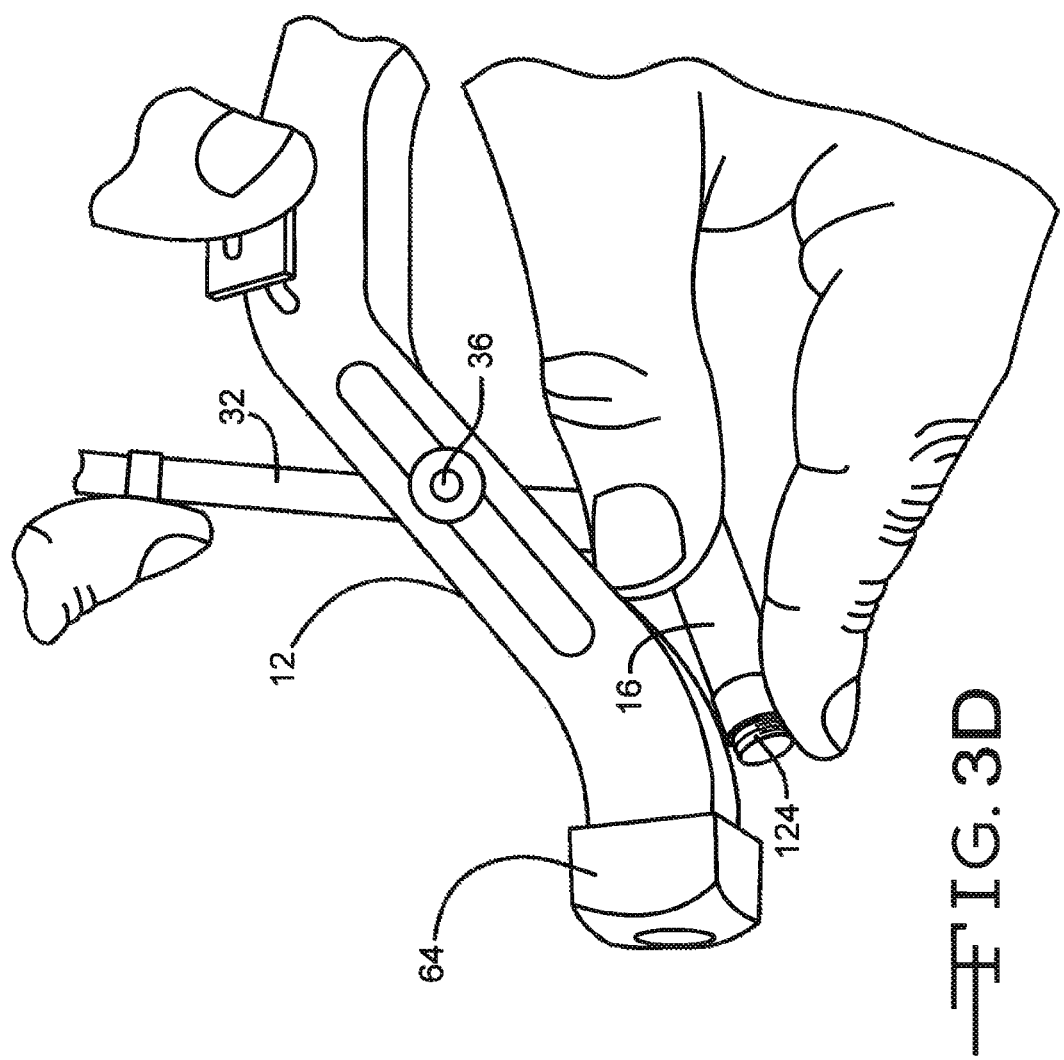

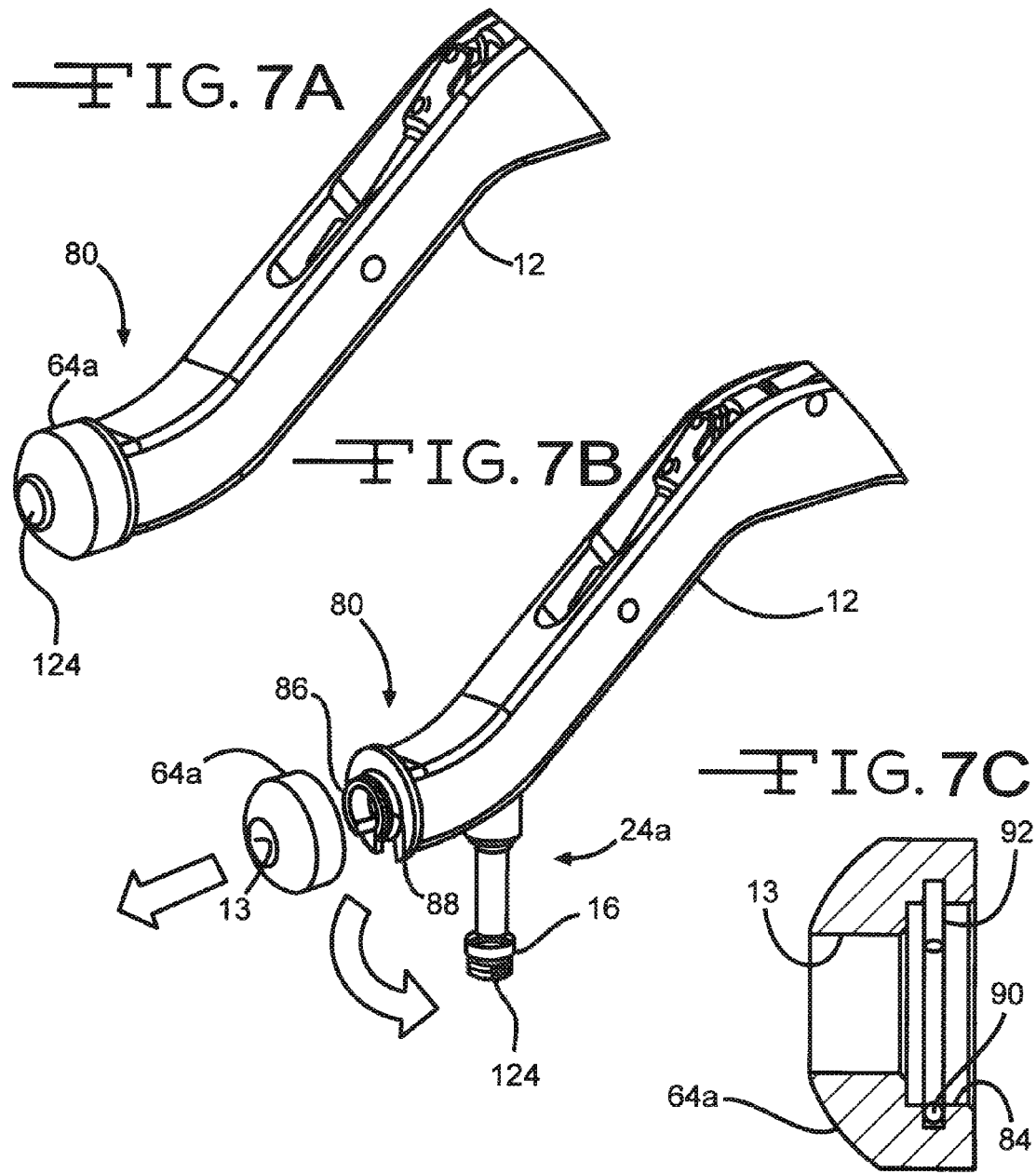

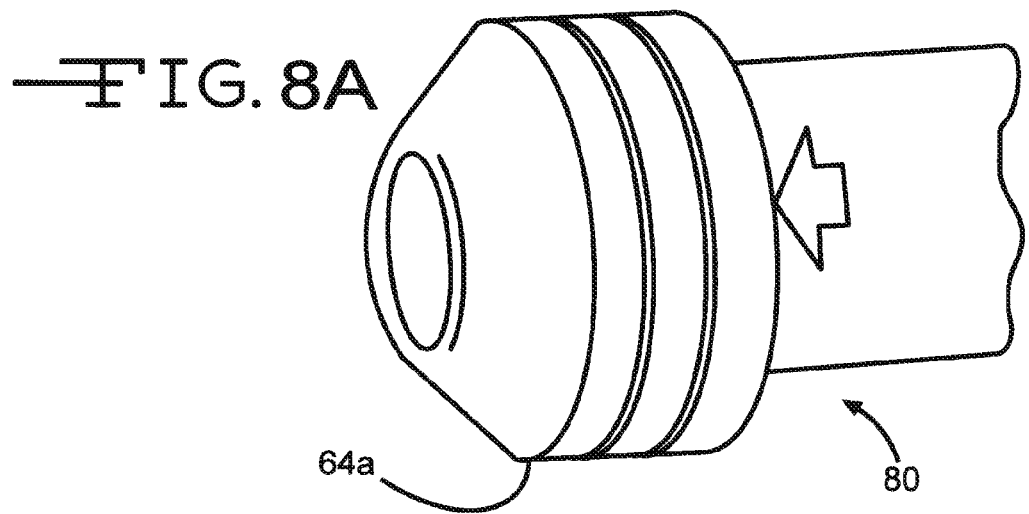
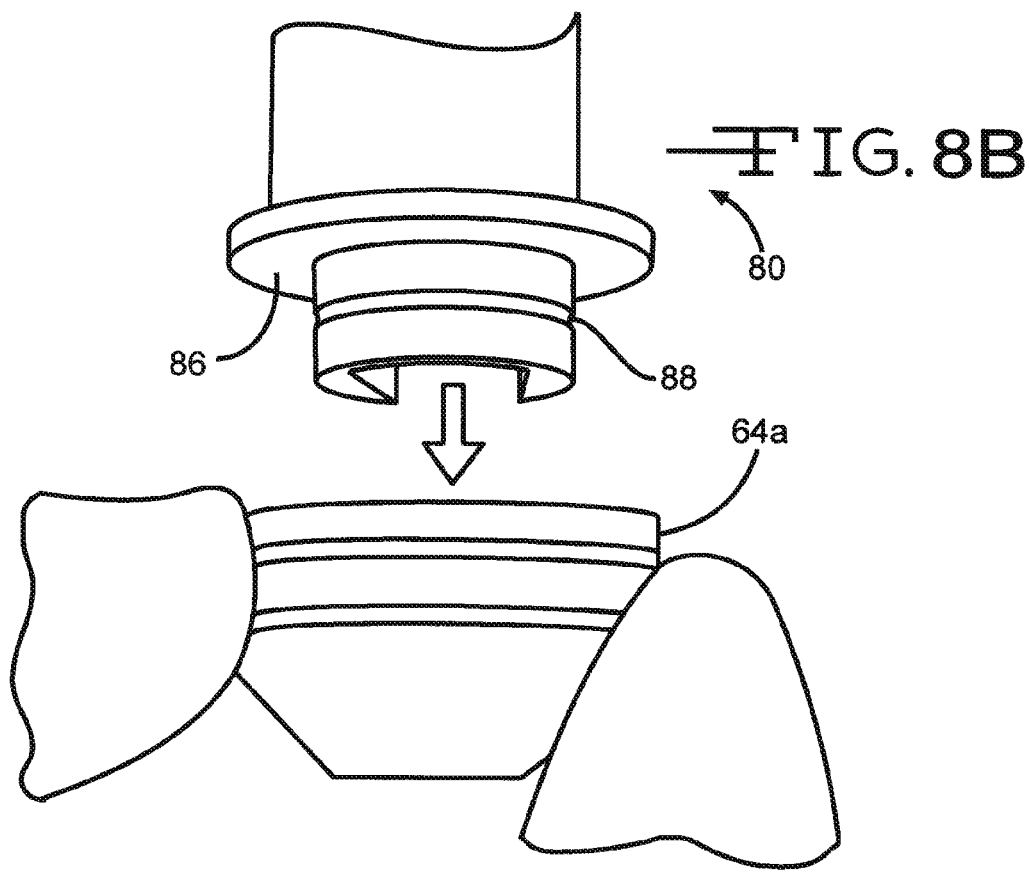

INSERTER FOR MINIMALLY INVASIVE JOINT SURGERY HAVING AN INTERCHANGEABLE PROSTHESIS ENGAGING PISTON

CROSS REFERENCE TO RELATED APPLICATIONS

This application is a divisional of application Ser. No. 11/741,868, filed Apr. 30, 2007 now U.S. Pat. No. 7,857,816, which claims priority to U.S. provisional application Ser. Nos. 60/746,061, filed on May 1, 2006, and 60/822,239, filed on Aug. 13, 2006, the contents of which are fully incorporated herein by reference and relied upon.

BACKGROUND OF THE INVENTION

This invention relates to surgical inserters such as impactors, for aiding in installing orthopedic prostheses, and, more particularly, to easily sterilizable inserters for installing acetabular implants in the acetabular socket.

Complicated mechanical devices have crevices and recesses that are difficult, if not almost impossible to clean with ease. Devices that are not properly cleaned and sterilized run the risk of disease transfer from patient to patient following the emergence of certain "prions" that are not killed by normal hospital sterilization and need to be physically removed by washing/rinsing.

Further, in surgical procedures in which access to the treatment site is limited, it is difficult to use current solutions without subjecting the patient to repeated abrasion and tissue trauma when inserting and extracting surgical instruments.

Further, the insertion of the implant is often problematic, and the orientation of the implant, particularly any fixing holes that might be pre-drilled in the implant is often critical to minimize recovery time of the patient. Still further, once the appropriate position of the implant is selected, it is often difficult to ensure that the position does not change upon insertion of the assembly through the incision.

Still further, a surgical inserter is needed having an interface which engages with the particular prosthesis that the surgeon selects for the particular needs of the patient. Thus, for the surgeon to be able to position and insert a variety of prostheses, he must very often have a corresponding number of inserters, given that the interface is not standardized.

What is needed therefore is an inserter that is easily adjustable, disassembleable, and cleanable. Further, what is needed is an inserter that enables the surgeon to better maneuver position and install an implant in a particular angular orientation. Still further, what is needed is an inserter wherein the interface alone, and not the entire inserter, may be changed out to enable the interfacing with the most appropriate prosthesis without the need for having a special inserter on hand for each particular interface.

SUMMARY OF THE INVENTION

An acetabular inserter aids a surgeon in controlling the installation of an acetabular cup prosthesis generally having a central, female aperture. The inserter has a housing which supports a drive train having, at a far end, an interchangeable prosthesis engaging interface (e.g., an interchangeable thread), and at the opposite end, a handle which facilitates turning of the drive train by the operator.

The inserter enables easy and controlled orientation of a prosthesis attached to its end, which is important because the prosthesis often has pre-drilled holes and thus, these must be properly positioned prior to fastening through these holes. Proper positioning may be dictated due to different length fasteners to engage with bone of varying thickness.

An objective of the invention is to be "easily cleaned" by quick and modular disassembly which enables access to all surfaces so that they can be cleaned, the reduction in number of small radius internal corners, crevices and small gaps and the absence of blind holes.

Another object of the invention is to provide an inserter which enables the implant to be locked in an angular orientation prior to installation of the implant.

Another object of the invention is to provide a dual mechanism that uses common components to lock the implant in place as well as to provide for easy disassembly for cleaning and sterilization.

Another object of the invention is to reduce the number of pieces and the risk that parts could be lost.

BRIEF DESCRIPTION OF THE DRAWINGS

The attached drawings represent, by way of example, different embodiments of the subject of the invention.

FIG. 1C is a perspective view of the inserter of the invention showing a one way catch mechanism.

FIG. 3B is a perspective view of the inserter of the invention, showing another step of disassembly for cleaning.

FIG. 3C is a perspective view of the inserter of the invention, showing a stage of disassembly for cleaning.

FIG. 3D is a perspective view of the inserter of the invention, showing a stage of re-assembly after cleaning.

FIGS. 7A and 7B are perspective views of (A) the housing of the present inserter with an interchangeable inserter head attached, and (B) with an interchangeable inserter head removed.

FIGS. 7C and 7D, respectively, are cross-sectional and perspective views of an inserter head.

FIGS. 8A and 8B illustrate the manual removal and attachment of an inserter head to the inserter end of the housing of the present invention.

DETAILED DESCRIPTION OF THE PREFERRED EMBODIMENTS

Figure 1A:
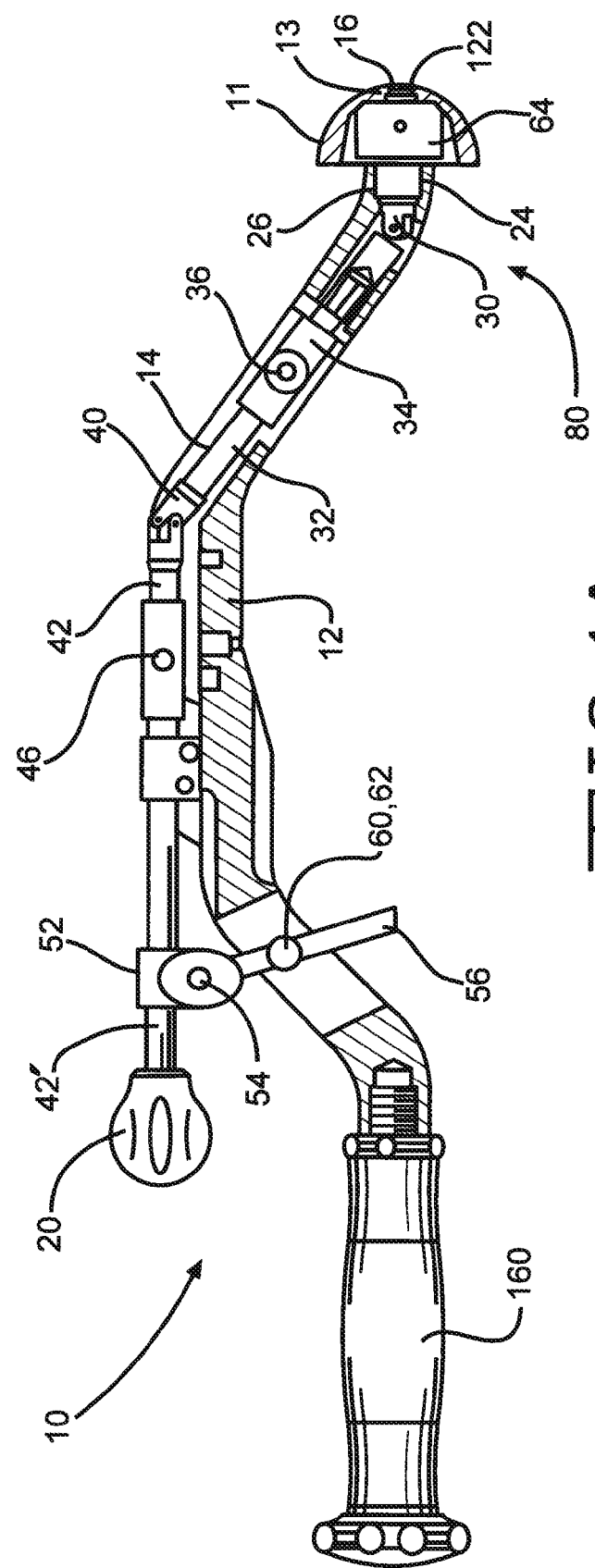
FIG. 1A is a cross-sectional side view of the inserter of the invention, including a side view of the drive train separated from the invention.
Figure 1B:
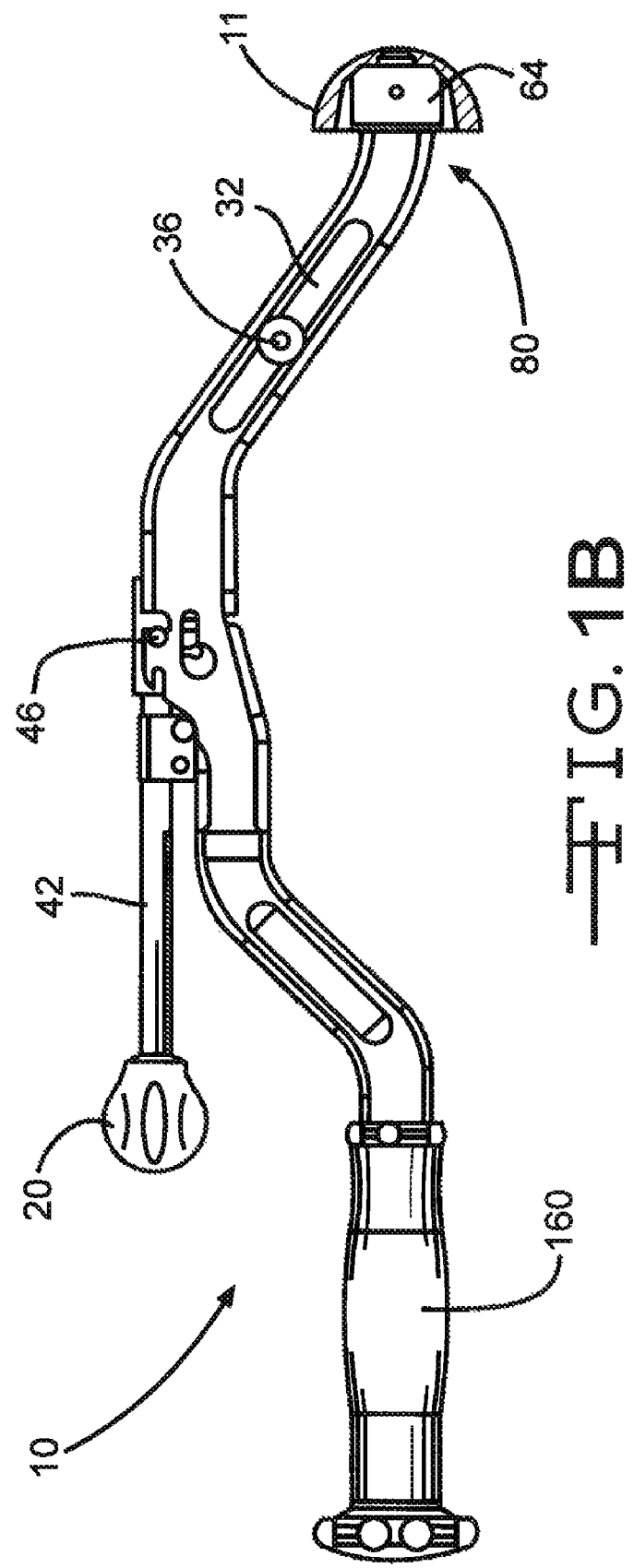
FIG. 1B is a side view of the inserter of the invention.

Referring now to FIGS. 1A-1C, an acetabular inserter 10 is provided to aid the surgeon in controlling the installation of an acetabular cup prosthesis 11 having a central, female aperture 13. The inserter 10 has a housing 12 which encloses a drive train 14 having, at a far end, a prosthesis engaging, interchangeable interface 16 (preferably having a prosthesis engaging thread), and at the opposite end, a knob 20 which facilitates turning of the drive train by the operator. The housing 12 may be C-shaped, as shown, in order to minimize the invasiveness of the surgery by better clearing anatomical structures and tissue.

The interface 16 is cut on a boss 22 which is releasably engageable with a linkage 24 which slides in an axial hole 26 in the housing 12. The interface 16 is preferably threaded. The piston 24 is connected by way of a first U-joint 30 to a lever 32 which slides in a pivoting sleeve 34 fixed to the housing 12 via a pivot 36. The lever 32 is connected via a second U-joint 40 to a second pivoting lever 42 which is fixed to pivot in a catch 44 on a pivot pin 46. The catch 44 is essentially a divot or a seat cut into the housing 12, against which the pivot pin 46 of the lever 42 is captured when a slide 50 is slid over the pin when engaged against the seat.

FIG. 1A includes a side view of the drive train of the invention. A slideable sleeve 52 slides over the lever 42 and has a trunion 54 to which a rod 56 is pivotally attached. The rod 56 passes through a one-way catch 60 in the housing 12. The one-way catch 60 can be a captured split wedge sleeve 62 having an inner diameter that just matches the outer diameter of the rod 56 and which is captured in a recess having a matching conical surface that surrounds the sleeve so as to allow the rod 56 to slide into the housing 12, but to prevent the rod from sliding out of the housing unless an unlock lever (not shown) is activated, such lever merely lifting the sleeve 62 out of engagement with the conical surface so as not to lock and to permit the rod to back out of the housing. Any number of alternative one-way lock devices may be used however, the selection of which being within the skill of a person of ordinary skill in this field.

Referring now to FIG. 1C, an alternative embodiment of the one way catch mechanism 60 is shown. In this embodiment, the rod 56 passes through a one-way catch 60 in the housing 12. The one-way catch 60 has an inner recess that matches the outer diameter of the rod 56. The inner recess has a ratchet pawl (not shown) that locks against one way ratchet teeth 67 so as to allow the rod 56 to slide into the housing 12, but to prevent the rod from sliding out of the housing unless an unlock lever 68 is activated, such lever merely pulling the pawl away from the teeth to permit the rod to back out of the housing.

A polymeric inserter head 64 is molded over the end of the housing 12, to absorb the impact stresses incurred during use of the inserter. The head 64 is selected so as to have good frictional characteristics as well. Nevertheless, a metal, non-molded head may also be used with satisfactory results.

Figure 2A:
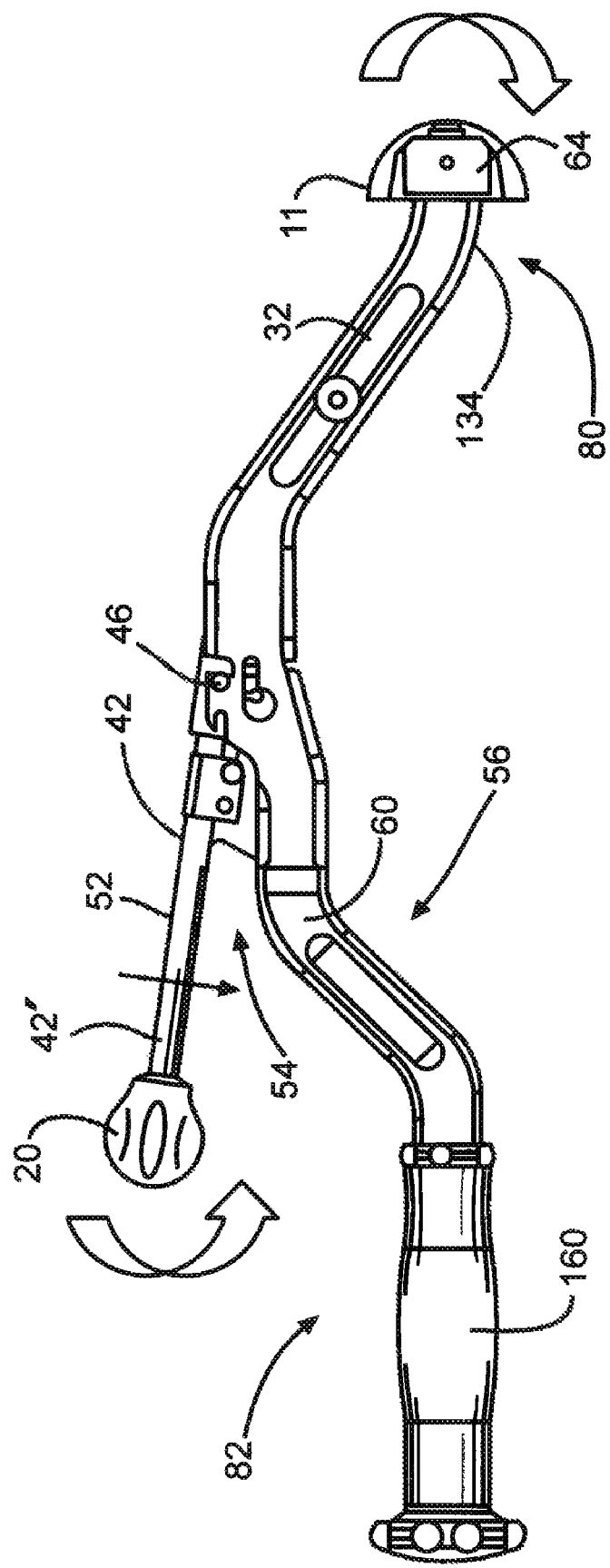
FIG. 2A is an operational side view of the inserter of the invention.
Figure 2B:
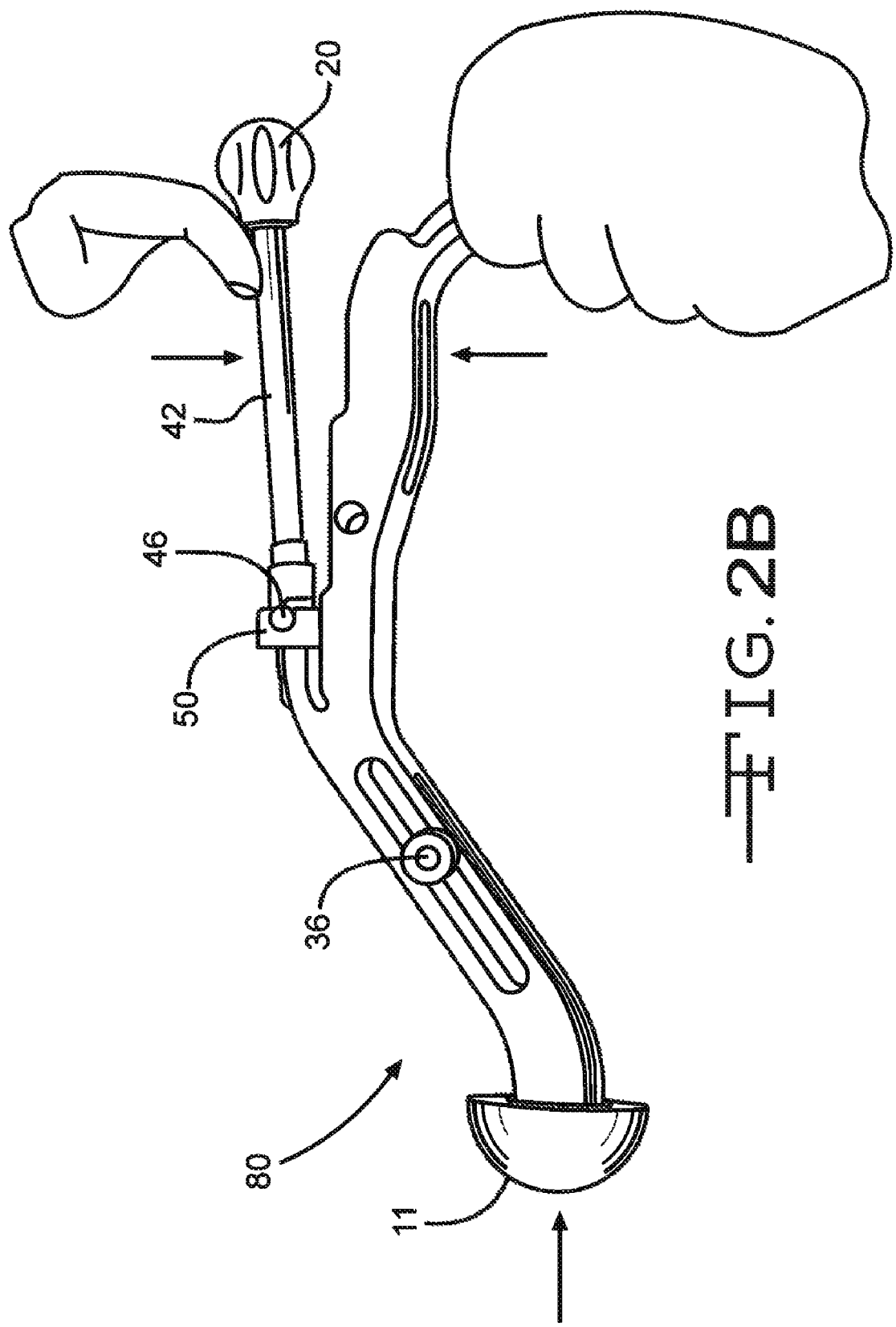
FIG. 2B is an operational hack view of the inserter of the invention.
Figure 3A:
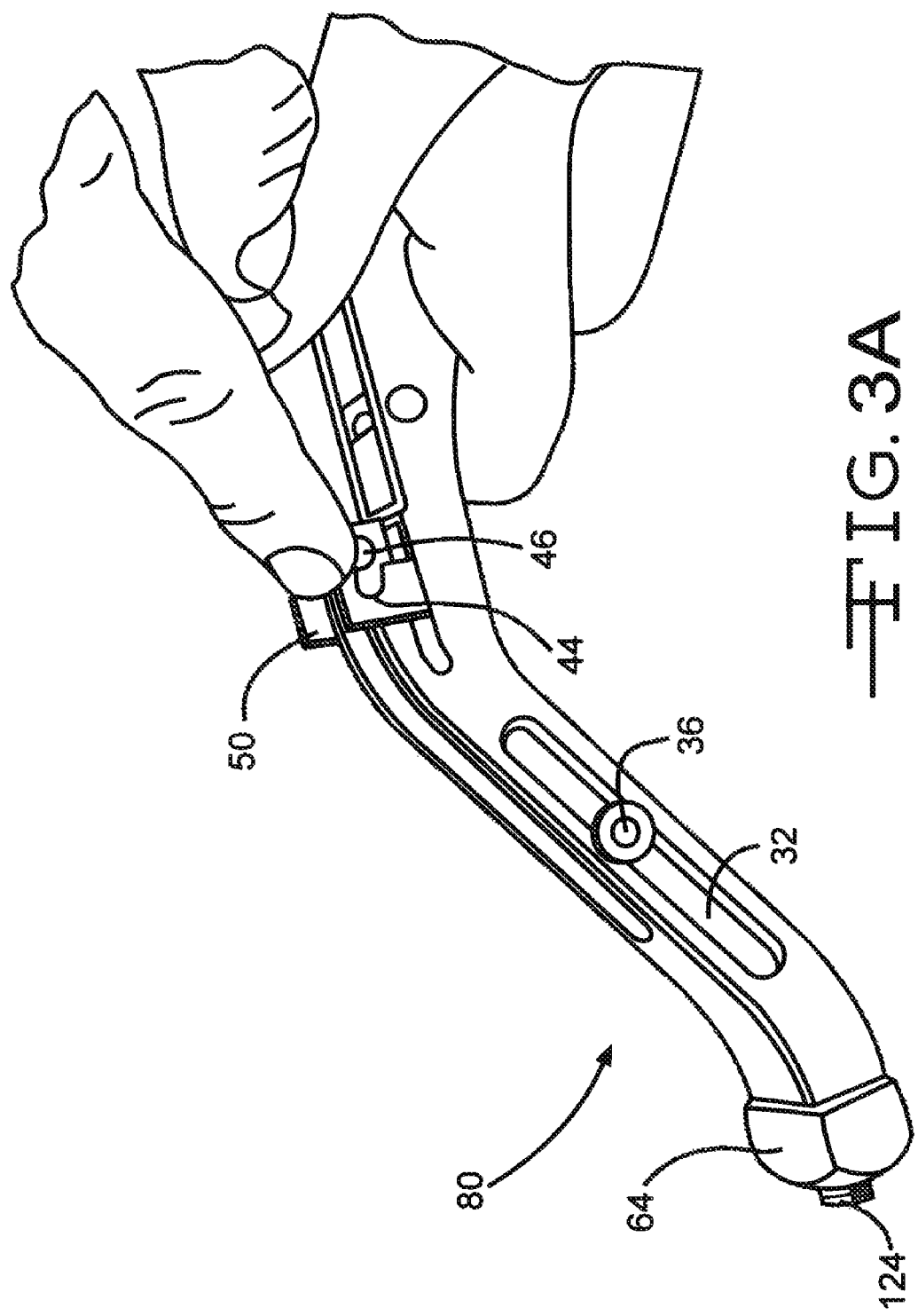
FIG. 3A is a perspective view of the inserter of the invention, showing a step of disassembly for cleaning.

Referring now to FIGS. 2A-2B, in operation, the interface 16 (preferably threaded) of the piston 24 is engaged with the hole 13 of the prosthesis 11. The operator may rotate the knob 20 about its axis to turn the drive train 14 in order to interface the piston 24 into the hole 13 of or to orient the prosthesis in what he believes to be a correct or an initial position. Then, an end 42' of the lever 42 is urged downwardly toward the housing 12. Such downward movement acts through the drive train 14 to draw the piston 24 into the housing 12, and thus to cause the inner surface of the prosthesis 11 to be drawn against the head 64 so as to create a normal force between the inside of the prosthesis and the head so as to prevent rotation of the prosthesis 11 relative to the housing 12. The operator may use the one way locking Mechanism 62 to lock the lever 42 in a position so as to lock the prosthesis 11 against the head 64, thus enabling the surgeon to pre-set and lock the position of the prosthesis prior to the installation thereof. Note that orientation of the prosthesis 11 is important because the prosthesis often has pre-drilled holes 4 (shown in FIG. 4A) and thus, these must be properly positioned prior to fastening through these holes.

The "easily cleaned" objective of the invention enables access to all surfaces that they can be cleaned (parts covering another part can be moved or removed to expose all surfaces), the reduction in number of small radius internal corners, crevices and small gaps and the absence of blind holes.

Referring now to FIGS. 3A-3D, in the embodiment shown, the device 10 is disassembled for cleaning by simply sliding the slide 50 back so as to release the pivot 46 and then lift the drive train 14 out of the housing but allow it to remain pivotally connected at pivot 36. As the drive train 14 is pivoted, the piston 16 is drawn out of the hole 26 in the housing 12. To reassemble after cleaning, the piston 16 is reinserted into the hole 26 and the drive train 14 is rotated back into position, with the one way locking mechanism entering its receiver and the pivot 46 again entering into the catch 44. The slide 50 is then slide over the pivot 46 and the inserter 10 is again ready for use.

Figure 4A:
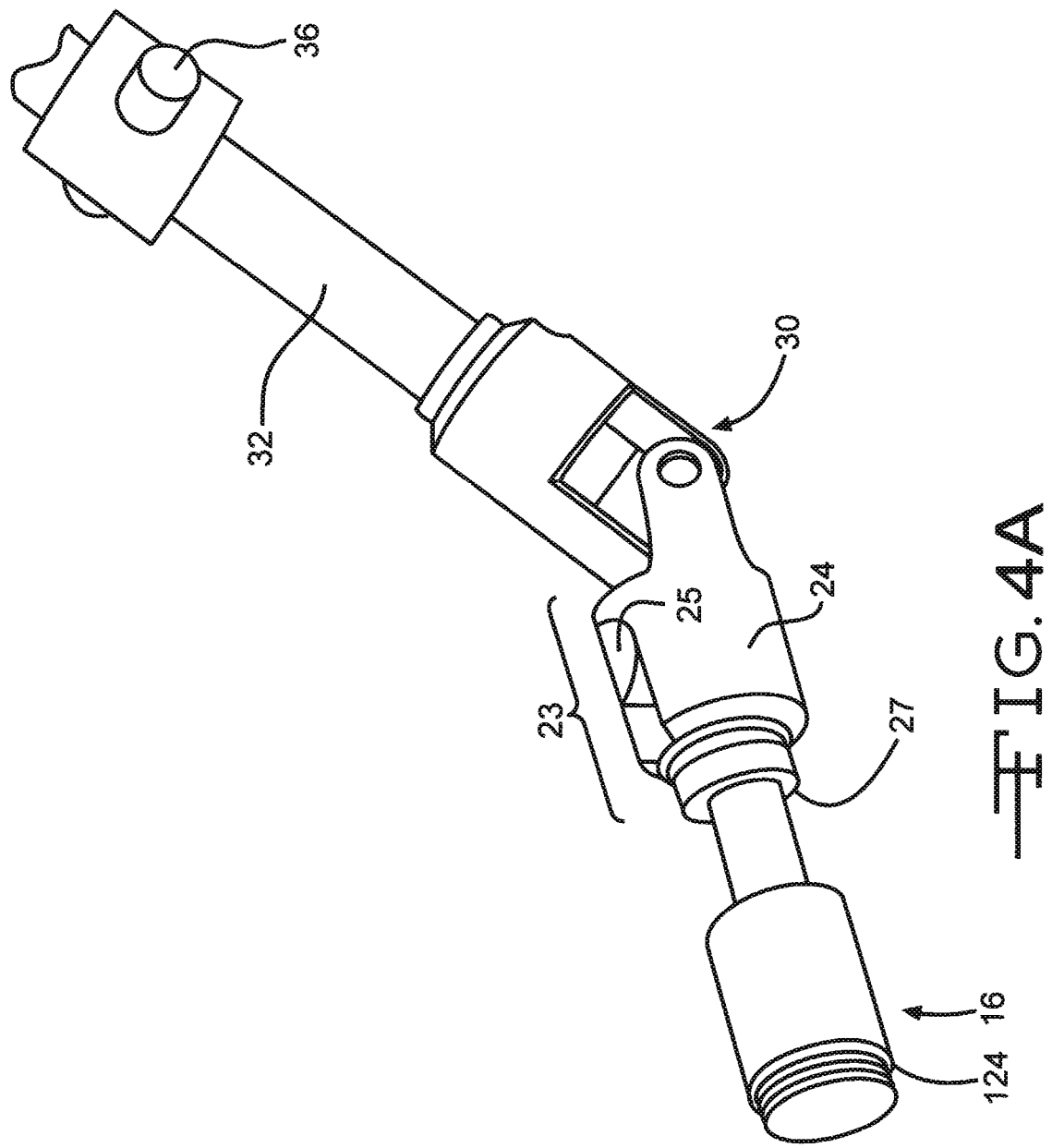
FIG. 4A is a perspective view of the interchangeable interface of the invention, assembled together.

Referring now to FIG. 4A, the interchangeable piston 16 is shown joined to the drive train 14 so as to turn as a unit therewith across a bend through the universal joint 30. The piston 16 has an interface end that is preferably threaded with threads 124 to match the threads of a particular prosthesis 11. On an opposite end thereof, the piston 16 has a releasable connection mechanism 23 comprising a dove tail 25 (shown most clearly in FIGS. 4B and 4D) and a threaded ferrule 27.

Figure 4B:
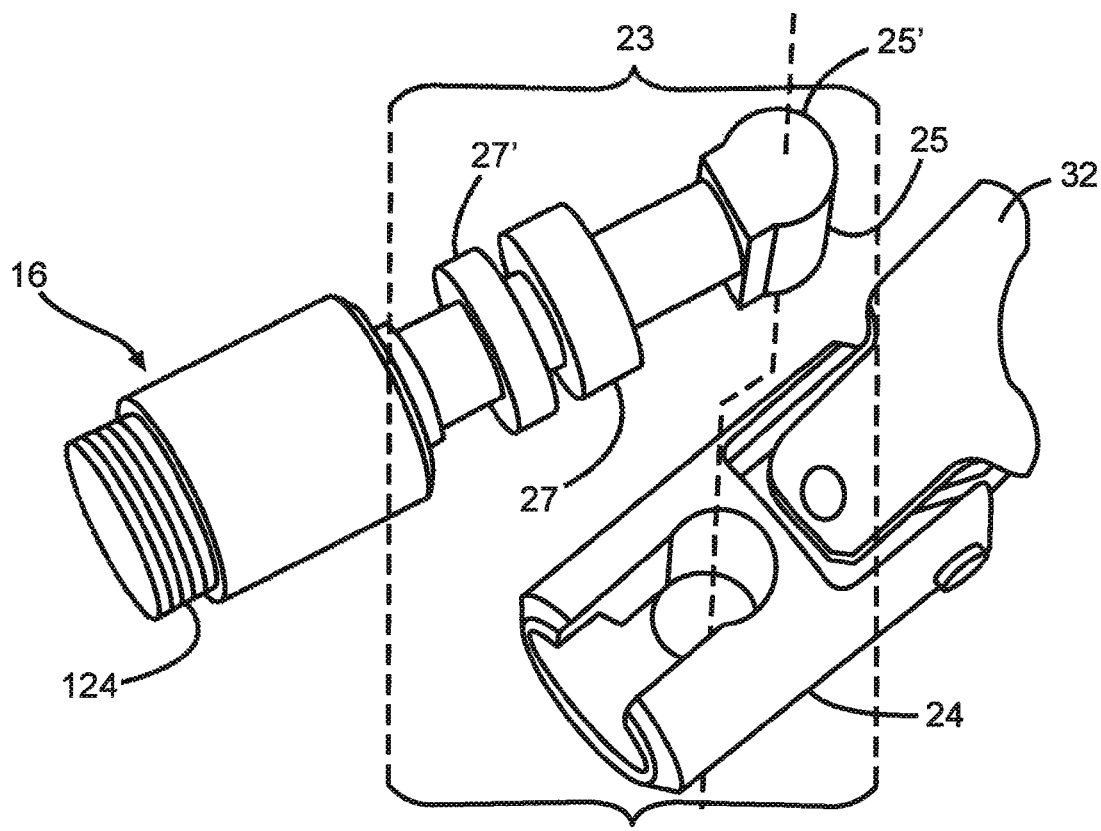
FIG. 4B is a close up perspective view of the interchangeable interface, disassembled.

Referring now to FIG. 4B, the dove tail 25 is formed so as to have a bulbous profile that slides into and mates with the linkage 24 which has a corresponding transverse aperture which cradles the dove tail 25 once it is captured in the hole 26 in the housing 12. Note that the extreme ends 25' of the dovetail 25 are cylindrical to provide surface contact in sliding with the hole 26.

Figure 4C:
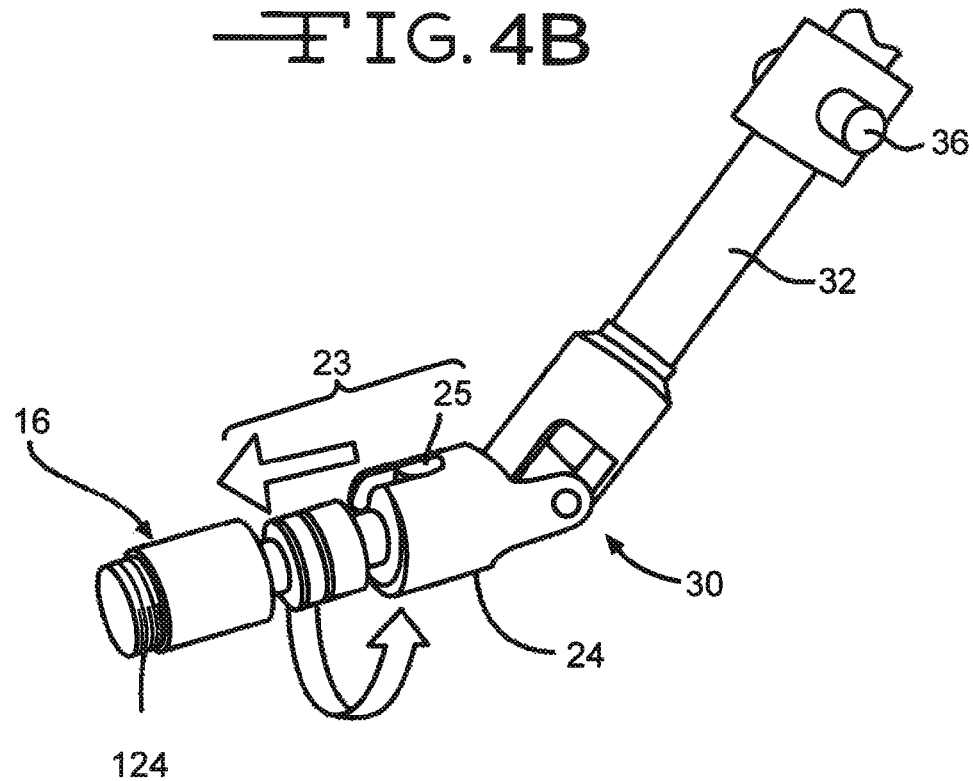
FIG. 4C is a perspective view illustrating a first step of disassembly of an assembled interchangeable interface.

Referring now to FIG. 4C, the piston 16 may be removed by unthreading the ferrule 27 by hand (for this purpose, the knurled annular portion 27' is useful) so as to release a wedging force generated upon torquing the ferrule at assembly. The wedging force is generated between the curved cylindrical walls of the aperture of the linkage 24 and the corresponding curved walls of the dove tail 25. Note, however, wedging is not required, but merely ensures an integral connection of the piston 16 to the linkage 24.

Figure 4D:
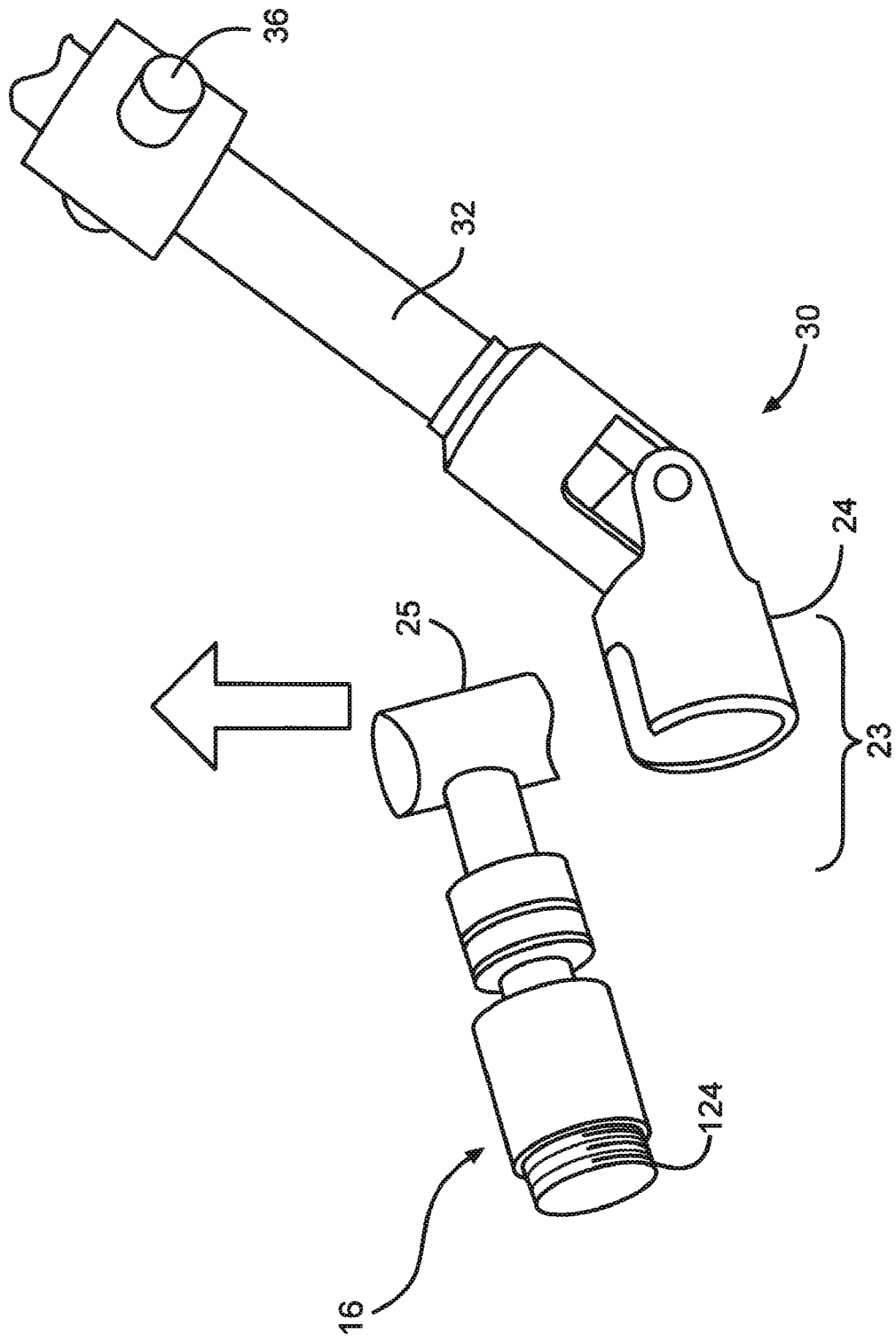
FIG. 4D is a perspective view showing the removal of the interchangeable interface, from a dove tail groove in the drive shaft assembly.

Referring now to FIG. 4D, after the torque is released, this drawing is a perspective view showing the removal of the interchangeable interface, from a dove tail groove in the drive shaft assembly.

Figure 5:
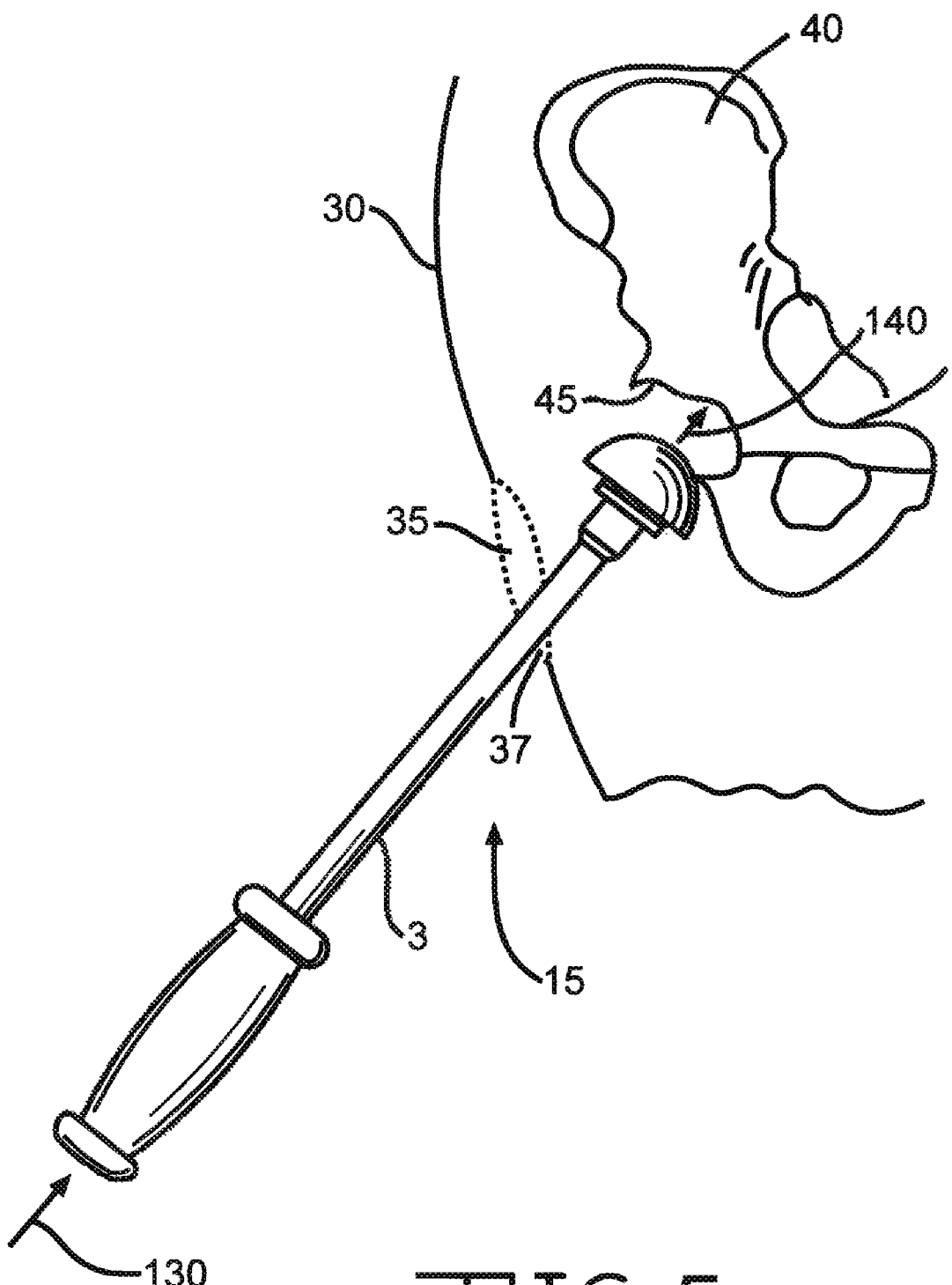
FIG. 5 is a schematic view of a prior art inserter.
Figure 6:
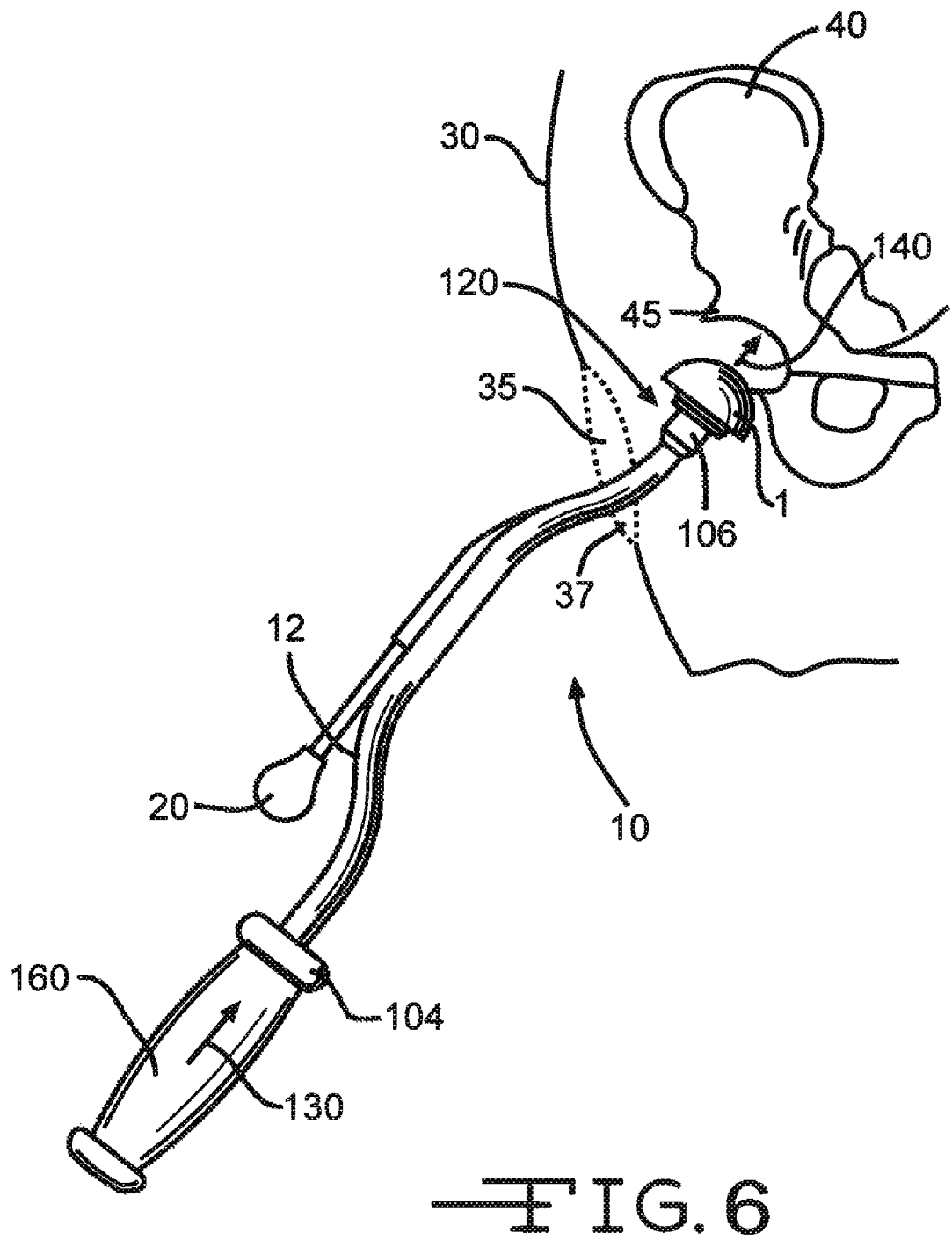
FIG. 6 is a schematic view of the inserter of the invention in operation.

Referring to FIGS. 5-6, a prior art inserter 15 and the present invention inserter 10, respectively, are shown passing through a miniature incision 35 in the patient's skin 30. In FIG. 5, the inserter 15 is shown approaching the acetabulum 40 in an orientation desirable to ream the socket 45. The difficulty with the prior art spindle 15 is shown as the shaft 3 impinges on the miniature incision 35 at edge of the incision 37. The current surgical protocols are being pushed to the limits and the incision sizes are being reduced in the hopes of increasing the patient's speed to recovery. In some cases surgeons are using a two-incision approach, one to reach the acetabulum and the other to reach the femur. Either one incision or two incision techniques demand less trauma to the patient requiring the instruments to be more optimally designed to make up for the lack of operating space. FIG. 6 shows the present invention inserter 10, which has a bent housing 12 containing the drive train 14.

It is important to place the bends in the housing at critical locations to pass through the miniature incision without impinging on the skin 30 at 37 while still maintaining the same surgical protocol. The reason why the drive end 104 and the holding mechanism 120 need to be in line or on parallel axis is so that the applied force 130 results in an axial motion 140. This allows the surgeon to maintain the existing technique since inherently inserter 15 in FIG. 5 would give the same result since it has a straight drive shaft 3. This allows the surgeon to apply a load directly along the path of reaming.

It should be noted that a second head (not shown) can be mounted onto the front of the device 10, the head formed so as to conform with a surface of an acetabular cup liner, in order to enable the device to seat a liner as well as the cup.

The attached drawings represent, by way of example, different embodiments of the subject of the invention.

In operation, the prosthesis first is placed over or threaded onto the collet 120 via a threaded hole 122. In a second step, the prosthesis 11 is oriented with respect to the form of the inserter 10, in order to minimally impact soft tissue. In a third step, the handle 160 of the inserter 10 is gripped and the prosthesis 11 placed through the incision 35. In a fourth step, the inserter 10 is used to impact the prosthesis 11 in place by impacting a rear portion of the handle 160 with a mallet, for example. Optionally, with the current design, it is envisioned that the prosthesis 11 be inserted into the incision 35 as a first step, potentially taking advantage of being able to more freely maneuver it into the incision and to roughly position it prior to inserting the collet 120 of the inserter 10 into a mating hole in the tool head. If this optional procedure is used, the knob 20 of the inserter may then be turned by the operator to actuate the opening of the collet 120 and thus the fixing on the end of the inserter 10. These optional steps substitute for the above mentioned four steps. In a fifth step, the knob 20 is turned in an opposite direction in order to release the prosthesis 11. In a final step, the inserter 10 is removed from the incision 35.

Figure 7D:
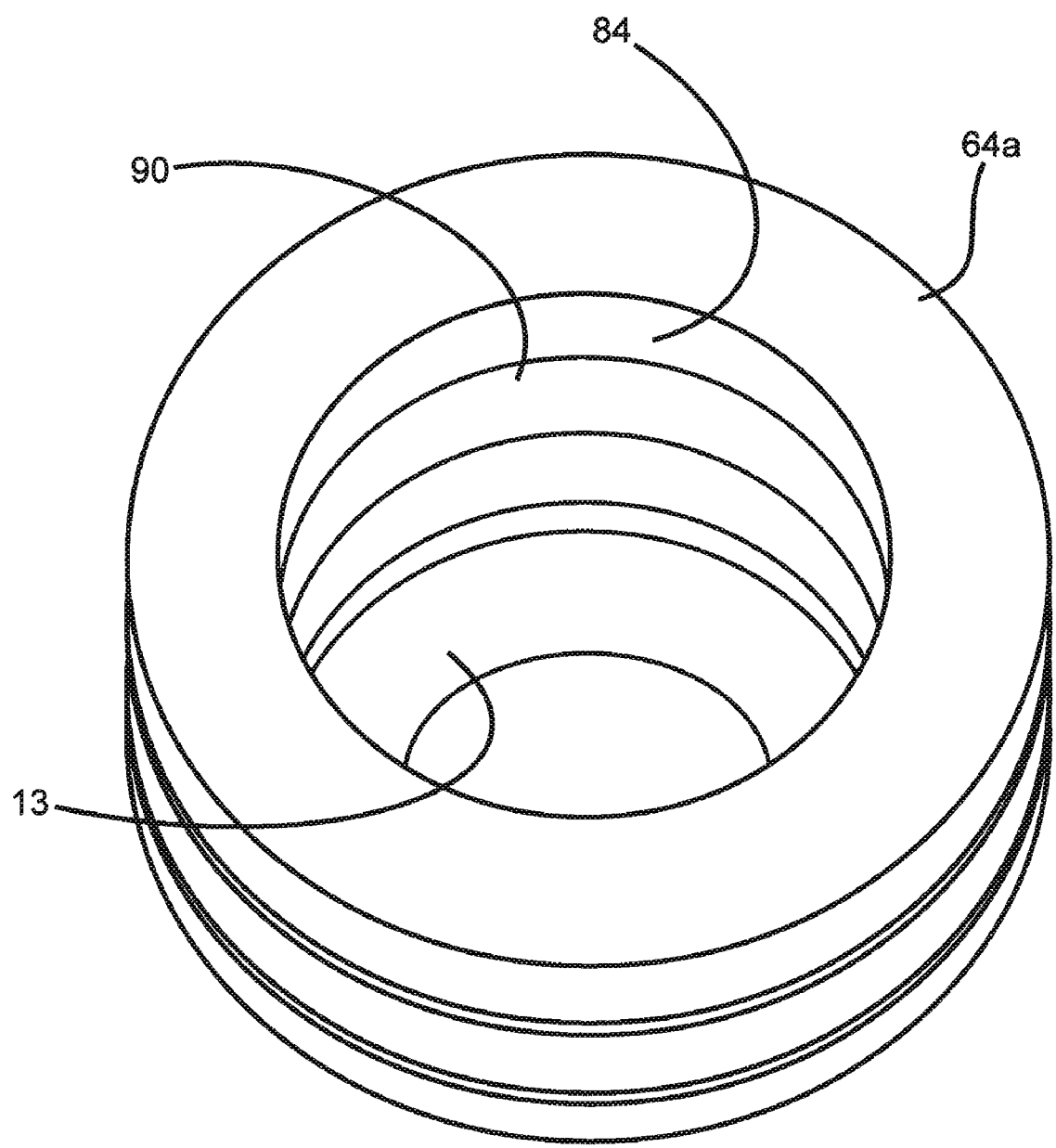

As noted above, in another preferred embodiment illustrated in FIGS. 7A through 9, the present inserter 10 has an inserted head 64a that is removable and can be interchanged with an alternative inserter head that is configured to mate with a corresponding alternative prosthesis device 11. FIG. 7A illustrate this alternative embodiment with the interchangeable inserter head 64a in place on the inserter end 80 of the housing 12 of the present inserter 10 in a fully assembled condition. In FIG. 7B, the inserter head 64a has been removed from the inserter end 80 of the housing 12. FIGS. 7C and 7D are cross-sectional and perspective views, respectively, of the inserter head 64a showing a head recess 84 for closely receiving a housing boss 86 disposed at the inserted end 80 of the housing 12. A retainer means holds the inserter head 64a in place on the housing boss 86 when it is attached to the housing 12. In the embodiment illustrated the retainer means comprises a detent groove 88 on the outer surface of the housing boss 86, and a snap ring 90 disposed in a ring groove 92 in the inner circumference of the head recess 84. In practice, when the housing boss 86 is initially received into the head recess 84, the snap ring 90 is forced into an expanded condition until the ring 90 snaps into the detent groove 88 on the outer surface of the housing boss 86 to hold the inserted head 64a in place on the boss 86. As illustrated in FIGS. 8A and 8B, the inserter head 64a is removed by manually pulling the head 64a away from the boss 86 and overcoming the bias retaining the snap ring 90 in the detent groove 88.

Figure 9A:
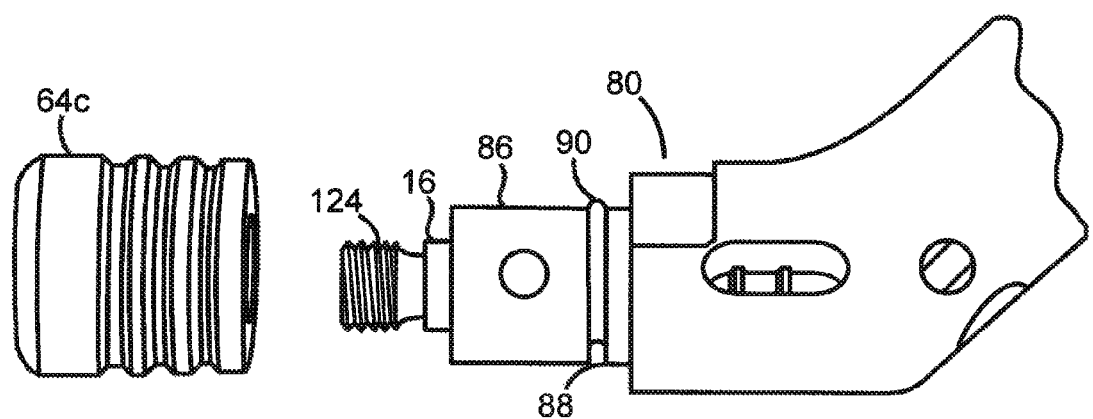
FIGS. 9A and 9B are, respectively, (A) an assembled view and (B) an exploded view of an alternative inserter head disposed on the housing boss.
Figure 9B:
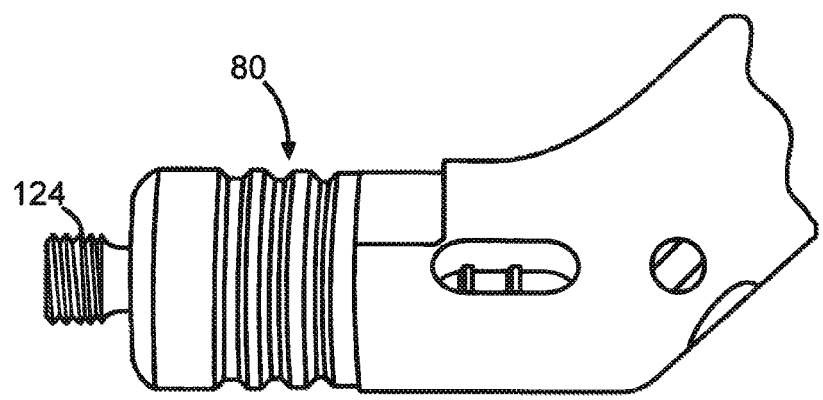

FIGS. 9A and 9B are (A) an assembled view and (B) an exploded view of an alternative inserter head disposed on the housing boss. In the exploded view, an alternative interchangeable inserter head 64c is disposed at the inserter end 80 of the housing. The view is exploded to show the details of the components of a detent mechanism disposed on the housing boss 86.

The "easily cleaned" objective of the invention 10 enables access to all surfaces that they can be cleaned (parts covering another part can be moved or removed to expose all surfaces), the reduction in number of small radius internal corners, crevices and small gaps and the absence of blind holes.

In another advantage, it is simple to select a desired orientation of the prosthesis device 11, which enables the device to be locked in an angular orientation prior to installation. Additionally, due to drawing of the prosthesis 11 against and in close contact with the inserter head 64, contact between the two is robust as it is made with minimal play or gaps there between, ensuring good support during impaction.

In an advantage, the inserter 10 is simple and easy to use, without complex and possibly confusing locks activated with the thumb. It is simple to select a desired orientation of the prosthesis 11.

In another advantage, due to the drawing of the prosthesis 2 against the impaction head 40, the connection between the prosthesis 11 is robust as the connection is made without any play or gaps therebetween, ensuring good support during impaction.

An objective is to provide an inserter 10 that is easy to disassemble and for which the disassembly is easy to learn.

Another object of the invention is to provide a dual mechanism that uses common components to lock the implant in place as well as to provide for easy disassembly for cleaning and sterilization.

Another object of the invention is to minimize the number of pieces and the risk that parts could be lost.

The object of the invention is to provide an inserter 10 which enables the implant to be locked in an angular orientation prior to installation of the implant.

While one or more preferred embodiments of the present invention have been described, it should be understood that various changes, adaptations and modifications may be made without departing from the spirit of the invention and the scope of the appended claims.

What is claimed is:

1. An inserter for aiding a surgeon in controlling a prosthesis during installation of the prosthesis, the inserter comprising:
   a) an inserter head having a longitudinally extending bore therethrough;
   b) a housing attached to the inserter head, the housing comprising a proximal housing end and a distal housing end supporting the inserter head;
   c) a drive train at least partially housed inside the housing, the drive train comprising:
      i) a first lever comprising a first lever proximal end spaced apart from a first lever distal end;
      ii) a first sleeve pivotably connected to the housing, wherein the first lever is in a slidable relationship with a first opening in the sleeve disposed at an intermediate location between the first lever proximal end and the first lever distal end;
      iii) a second lever comprising a second lever proximal end located adjacent to the proximal housing end and spaced apart from a second lever distal end, wherein the second lever is pivotably supported by the housing;

iv) a linkage comprising a linkage proximal end spaced apart from a linkage distal end located adjacent to the distal housing end;

v) a piston comprising a piston proximal end spaced apart from a piston distal end that is configured to be connectible to a prosthesis, vi) wherein the second lever distal end is in a first universal joint relationship with the first lever proximal end, and wherein the first lever distal end is in a second universal joint relationship with the linkage proximal end, and wherein the piston proximal end includes a ferrule that is threadable into a wedging relationship with the linkage distal end and the piston distal end extends through the bore in the inserter head; and d) wherein the second lever proximal end is manipulable from a first position spaced from the housing to a second position spaced closer to the housing than the first position to cause the second lever to pivot with respect to the housing and thereby move the second lever distal end away from the distal housing end and to further cause the first lever connected to the linkage which in turn is connected to the piston to move away from the distal housing end as the first lever moves along the first opening in the first sleeve as the first sleeve pivots on the housing to thereby cause the linkage to move in a proximal direction as the piston moves along the longitudinal bore in the inserter head with the piston distal end moving from a first piston position spaced from the inserter head to a second piston position closer to the inserter head than the first piston position, and e) wherein with the piston in the first piston position, the ferrule of the piston is unthreadable from its wedging relationship with the linkage to enable the piston to be separable from the linkage such that the linkage is then configured for threadingly engaging a second piston with a second ferrule that is threadable into a wedging relationship with the linkage.

2. The inserter of claim 1 wherein the housing has at least one bend deviating from a longitudinal axis extending through the proximal housing end and the distal housing end, thereby permitting the housing to avoid anatomical structures or tissue during use in surgery.

3. The inserter of claim 2 wherein the first universal joint relationship between the first lever proximal end and the second lever distal end and the second universal joint relationship between the first lever distal end and the linkage help transmit torque through the at least one bend in the housing.

4. The inserter of claim 2 wherein the housing is C-shaped having at least two bends in order to minimize invasiveness of the surgery by better clearing anatomical structures and tissue.

5. The inserter of claim 1 wherein the proximal housing end comprises a handle.

6. The inserter of claim 1 wherein actuation of the drive train enables a user to draw a prosthesis connected to the piston distal end axially toward the distal housing end and against an impaction surface of the inserter head with sufficient friction therebetween to essentially lock the prosthesis in place.

7. The inserter of claim 1 wherein the drive train has a knob attached to the second lever proximal end, the knob enabling a user to orient the drive train including the piston distal end connectable to the prosthesis.

8. The inserter of claim 1 further comprising:

a) a second sleeve, wherein the second lever is in a slidable relationship with a second opening in the second sleeve disposed at an intermediate location between the second lever proximal end and the second lever distal end;

b) a first rod comprising a first rod proximal end pivotably connected to the second, sleeve and a first rod distal end adjustably connected to the housing in a one-way catch relationship; and c) wherein when the second lever proximal end is manipulated from the first position spaced from the housing to the second position spaced closer to the housing than the first position, that movement adjusts the one-way catch relationship between the first rod distal end and the housing as the second lever pivots with respect to the first rod proximal end and moves along the second opening in the second sleeve and as the second lever pivots on the housing with the linkage threadingly engaged with the piston moving in a proximal direction, thereby locking the piston in the piston second position with respect to the inserter head at a variable pressure exerted by the prosthesis against an impaction surface of the inserter head at the distal housing end.

9. The inserter of claim 8 wherein the proximal housing end comprises a handle and the one way catch relationship between the first rod and the handle prevents the first rod from disengaging from the housing unless an unlock lever is activated.

10. The inserter of claim 8 wherein the one-way catch relationship between the first rod and the handle is variable via a latch to permit release of the substantially friction tight relationship between the prosthesis and the inserter head.

11. The inserter of claim 8 wherein the one-way catch relationship between the first rod distal end and the housing is a ratchet relationship.

12. The inserter of claim 1 wherein the inserter head is covered by a shock-absorbing material that absorbs impact stresses incurred during impaction of the inserter.

13. A surgical kit including the inserter of claim 1, various pistons to fit different prostheses, a variety of prostheses, and a case to hold the inserter, pistons, and prostheses together in an organized fashion.

14. The inserter of claim 1 wherein the piston proximal end comprises a dove tail that is releasably matable to an aperture provided in the linkage.

15. The inserter of claim 14 wherein with the piston proximal end comprising the dove tail being releasably matable to the aperture provided, in the linkage, a first piston having a first piston distal end of a first size configured to be connectable to a first prosthesis is readily releasable from its mated relationship with the linkage distal end and replaceable with a second piston having a second piston distal end of a second size that is configured to be connectable to a second prosthesis of a second size different than the first size of the first prosthesis.

16. The inserter of claim 1 wherein the inserter head is provided in a snap-ring retention relationship with a housing boss located at the distal housing end, the inserter head being removable from the housing boss and replaceable with a second inserter head of a different size than the first inserter head.

17. The inserter of claim 1 wherein a slide is movable on the housing to a release position disengaged from retaining the pivotable relationship of the second lever with the housing so that the drive train except for the first sleeve supporting the first lever pivotably connected to the housing is separable from the housing and with the piston being removable from the bore in the inserter head.

18. The inserter of claim 1 wherein the second lever proximal end is manipulable in a rotational manner to rotate the drive train and transmit torque through at least one bend in the housing to thereby rotate the piston with respect to the inserter head supported at the distal end of the housing.

19. The inserter of claim 1 wherein with a prosthesis cup secured to the piston distal end, actuation of the drive train enables a user to draw the piston along the bore in the inserter head to thereby move the prosthesis cup against the inserter head into a substantially friction tight engagement therebetween with the prosthesis cup being incapable of rotational movement with respect to the inserter head.

20. An inserter for aiding a surgeon in controlling the installation of an orthopedic prosthesis, the inserter comprising:
  a) an inserter head having a longitudinally extending bore therethrough;
  b) a housing attached to the inserter head, the housing comprising a proximal housing end and a distal housing end supporting the inserter head;
  c) a drive train at least partially housed inside the housing, the drive train comprising:
    i) a first lever comprising a first lever proximal end spaced apart from a first lever distal end;
    ii) a first sleeve pivotably connected to the housing, wherein the first lever is in a slidable relationship with a first opening in the first sleeve disposed at an intermediate location between the first lever proximal end and the first lever distal end;
    iii) a second lever comprising a second lever proximal end located adjacent to the proximal housing end and spaced apart from a second lever distal end, wherein the second lever is pivotably supported by the housing;
    iv) a linkage comprising a linkage proximal end spaced apart from a linkage distal end located adjacent to the distal housing end;
    v) a piston comprising a piston proximal end spaced apart from a piston distal end that is configured to be connectible to a prosthesis,
    vi) wherein the second lever distal end is in a first universal joint relationship with the first lever proximal end, and wherein the first lever distal end is in a second universal joint relationship with the linkage proximal end, and wherein the piston proximal end includes a ferrule that is threadable into a wedging relationship with the linkage distal end and the piston distal end extends through the bore in the inserter head; and
  d) a prosthesis cup connected to the piston distal end;
  e) wherein the second lever proximal end is manipulable from a first position spaced from the housing to a second position spaced closer to the housing than the first position to cause the second lever to pivot with respect to the housing and thereby move the second lever distal end away from the distal housing end and to further cause the first lever connected to the linkage which in turn is connected to the piston to move away from the distal housing end as the first lever moves along the first opening in the first sleeve as the first sleeve pivots on the housing to thereby cause the linkage to move in a proximal direction as the piston moves along the longitudinal bore in the inserter head with the piston distal end moving from a first piston position spaced from the inserter head to a second piston position closer to the inserter head than the first piston position; and
  f) wherein this piston movement draws the prosthesis cup against the inserter head into a substantially friction tight engagement there between, and
  g) wherein with the piston in the first piston position, the ferrule of the piston is unthreadable from its wedging relationship with the linkage to enable the piston to be separable from the linkage such that the linkage is then configured for threadingly engaging a second piston with a second ferrule that is threadable into a wedging relationship with the linkage.

21. The inserter of claim 20 wherein the piston proximal end comprises a dove tail that is releasably eatable to an aperture provided in the linkage.

22. The inserter of claim 20 further comprising:
  a) a second sleeve, wherein the second lever is in a slidable relationship with a second opening in the second sleeve disposed at an intermediate location between the second lever proximal end and the second lever distal end;
  b) a first rod comprising a first rod proximal end pivotably connected to the second sleeve and a first rod distal end adjustably connected to the housing in a one-way catch relationship; and
  c) wherein when the second lever proximal end is manipulated from the first position spaced from the housing to the second position spaced closer to the housing than the first position, that movement adjusts the one-way catch relationship between the first rod distal end and the housing as the second lever pivots with respect to the first rod proximal end and moves along the second opening in the second sleeve and as the second lever pivots on the housing with the linkage threadingly engaged with the piston moving in a proximal direction, thereby locking the piston in the piston second position with respect to the inserter head at a variable pressure exerted by the prosthesis against an impaction surface of the inserter head at the distal housing end.

23. A surgical kit for minimally invasive surgery, the kit including:
  a) a case having recesses into which components of the kit may be conveniently stored until use;
  b) at least one orthopedic implant; and
  c) an inserter for aiding a surgeon in controlling the installation of the orthopedic implant, the inserter comprising:
    i) an inserter head having a longitudinally extending bore therethrough;
    ii) a housing comprising a proximal housing end and a distal housing end supporting the inserter head;
    iii) a first lever comprising a first lever proximal end spaced apart from a first lever distal end;
    iv) a first sleeve pivotably connected to the housing, wherein the first lever is in a slidable relationship with a first opening in the first sleeve disposed at an intermediate location between the first lever proximal end and the first lever distal end;
    v) a second lever comprising a second lever proximal end located adjacent to the proximal housing end and spaced apart from a second lever distal end, wherein the second lever is pivotably supported by the housing;
    vi) a linkage comprising a linkage proximal end spaced apart from a linkage distal end located adjacent to the distal housing end;
    vii) a piston comprising a piston proximal end spaced apart from a piston distal end that is configured to be connectible to a prosthesis,
    viii) wherein the second lever distal end is in a first universal joint relationship with the first lever proximal end, and wherein the first lever distal end is in a second universal joint relationship with the linkage proximal end, and wherein, the piston proximal end includes a ferrule that is threadable into a wedging relationship with the linkage distal end and the piston distal end extends through the bore in the inserter head; and d) wherein the second lever proximal end is manipulable from a first position spaced from the housing to a second position spaced closer to the housing than the first position to cause the second lever to pivot with respect to the housing and thereby move the second lever distal end away from the distal housing end and to further cause the first lever connected to the linkage which in turn is connected to the piston to move away from the distal housing end as the first lever moves along the first opening in the first sleeve as the first sleeve pivots on the housing to thereby cause the linkage to move in a proximal direction as the piston moves along the longitudinal bore in the inserter head with the piston distal end moving from a first piston position spaced from the inserter head to a second piston position closer to the inserter head than the first piston position, and e) wherein with the piston in the first piston position, the ferrule of the piston is unthreadable from its wedging relationship with the linkage to enable the piston to be separable from the linkage such that the linkage is then configured for threadingly engaging a second piston with a second ferrule that is threadable into a wedging relationship with the linkage.

24. The surgical kit of claim 23 wherein the piston proximal end comprises a dove tail that is releasably matable to an aperture provided in the linkage.

25. The surgical kit of claim 23 further comprising:
a) a second sleeve, wherein the second lever is in a slidable relationship with a second opening in the second sleeve disposed at an intermediate location between the second lever proximal end and the second lever distal end;
b) a first rod comprising a first rod proximal end pivotably connected to the second sleeve and a first rod distal end adjustably connected to the housing in a one-way catch relationship; and
c) wherein when the second lever proximal end is manipulated from the first position spaced from the housing to the second position spaced closer to the housing than the first position, that movement adjusts the one-way catch relationship between the first rod distal end and the housing as the second lever pivots with respect to the first rod proximal end and moves along the second opening in the second sleeve and as the second lever pivots on the housing with the linkage threadingly engaged with the piston moving in a proximal direction, thereby locking the piston in the piston second position with respect to the inserter head at a variable pressure exerted by the prosthesis against an impaction surface of the inserter head at the distal housing end.

26. The inserter of claim 23 wherein with the piston proximal end comprising the dove tail being releasably matable to the aperture provided in the linkage, a first piston having a first piston distal end of a first size configured to be connectable to a first prosthesis is readily releasable from its mated relationship with the linkage distal end and replaceable with a second piston having a second piston distal end of a second size that is configured to be connectable to a second prosthesis of a second size different than the first size of the first prosthesis.

27. An inserter for aiding a surgeon in controlling the installation of an orthopedic prosthesis, the inserter comprising:

a) an inserter head having a longitudinally extending bore there through;
b) a housing comprising a proximal housing end and a distal housing end supporting the inserter head; and
c) a drive train at least partially housed inside the housing, the drive train comprising:
  i) a first lever comprising a first lever proximal end spaced apart from a first lever distal end;
  ii) a first sleeve pivotably connected to the housing, wherein the first lever is in a slidable relationship with a first opening in the first sleeve disposed at an intermediate location between the first lever proximal end and the first lever distal end;
  iii) a second lever comprising a second lever proximal end located adjacent to the proximal housing end and spaced apart from a second lever distal end, wherein the second lever is pivotably supported by the housing;
  iv) a linkage comprising a linkage proximal end spaced apart from a linkage distal end located adjacent to the distal housing end;
  v) a piston comprising a piston proximal end spaced apart from a piston distal end that is configured to be connectible to a prosthesis,
  vi) wherein the second lever distal end is in a first universal joint relationship with the first lever proximal end, and wherein the first lever distal end is in a second universal joint relationship with the linkage proximal end, and wherein the piston proximal end includes a ferrule that is threadable into a wedging relationship with the linkage distal end and the piston distal end extends through the bore in the inserter head;
  vii) a second sleeve, wherein the second lever is in a slidable relationship with a second opening in the second sleeve disposed at an intermediate location between the second lever proximal end and the second lever distal end;
  vi) a first rod comprising a first rod proximal end pivotably connected to the second sleeve and a first rod distal end adjustably connected to the housing in a one-way catch relationship;
d) wherein the second lever proximal end is manipulable from a first position spaced from the housing to a second position spaced closer to the housing than the first position to cause the second lever to pivot, with respect to the housing and thereby move the second lever distal end away from the distal housing end and to further cause the first lever connected to the linkage which in turn is connected to the piston to move away from the distal housing end as the first lever moves along the first opening in the first sleeve as the first sleeve pivots on the housing to thereby cause the linkage to move in a proximal direction as the piston moves along the longitudinal bore in the inserter head with the piston distal end moving from a first piston position spaced from the inserter head to a second piston position closer to the inserter head than the first piston position, and
e) wherein when the second lever proximal end is manipulated from the first position to the second position, that movement adjusts the one-way catch relationship between the first rod distal end and the housing as the second lever pivots with respect to the first rod proximal end and moves along the second opening in the second sleeve and as the second lever pivots on the housing with the linkage threadingly engaged with the piston moving in a proximal direction, thereby locking the piston in the piston second position with respect to the inserter head; and f) wherein such piston movement enables a user to draw the prosthesis cup against the inserter head into a substantially friction tight engagement there between that is lockable by the one-way catch relationship between the first rod distal end and the housing, and g) wherein with the piston in the first piston position, the ferrule of the piston is unthreadable from its wedging relationship with the linkage to enable the piston to be separable from the linkage such that the linkage is then configured for threadingly engaging a second piston with a second ferrule that is threadable into a wedging relationship with the linkage.

28. The inserter of claim 27 wherein the piston proximal end comprises a dove tail that is releasably matable to an aperture provided in the linkage.

29. The inserter of claim 28 wherein with the piston proximal end comprising the dove tail being releasably matable to the aperture provided in the linkage, a first piston having a first piston distal end of a first size configured to be connectable to a first prosthesis is readily releasable from its mated relationship with the linkage distal end and replaceable with a second piston having a second piston distal end of a second size that is configured to be connectable to a second prosthesis of a second size different than the first size of the first prosthesis.

30. An inserter for aiding a surgeon in controlling a prosthesis during installation of the prosthesis, the inserter comprising:

a) an inserter head having a longitudinally extending bore therethrough;

b) a housing attached to the inserter head, the housing comprising a proximal housing end and a distal housing end supporting the inserter head;

c) a drive train at least partially housed inside the housing, the drive train comprising:
  i) a linkage comprising a linkage proximal end spaced apart from a linkage distal end located adjacent to the distal housing end;
  ii) a piston comprising a piston proximal end spaced apart from a piston distal end that is connectible to a prosthesis, wherein the piston includes a ferrule that is threadable into a wedging relationship with the linkage; and d) wherein a proximal end of the drive train is manipulable from a first position spaced from the housing to a second position spaced closer to the housing than the first position to cause the linkage connected to the piston to move in a proximal direction as the piston moves along the longitudinal bore in the inserter head with the piston distal end moving from a first piston position spaced from the inserter head to a second piston position closer to the inserter head than the first piston position, and e) wherein with the piston in the first piston position, the piston ferrule is unthreadable from its wedging relationship with the linkage to enable the piston to be separable from the linkage such that the linkage is then configured for threadingly engaging a second piston with a second ferrule that is configured to be threadable into a wedging relationship with the linkage.

31. The inserter of claim 30 wherein the housing has at least one bend deviating from a longitudinal axis extending through the proximal housing end and the distal housing end.

32. The inserter of claim 30 wherein the drive train has a knob that enable a user to orient the drive train including the piston distal end.

33. An inserter for aiding a surgeon in controlling a prosthesis during installation of the prosthesis, the inserter comprising:

a) an inserter head having a longitudinally extending bore therethrough;

b) a housing attached to the inserter head, the housing comprising a proximal housing end and a distal housing end supporting the inserter head;

c) a drive train at least partially housed inside the housing, the drive train comprising a piston comprising a piston proximal end spaced apart from a piston distal end that is connectible to a prosthesis, wherein the piston includes a ferrule that is threadable into a wedging relationship with a distal end of the drive train; and d) wherein a proximal end of the drive train is manipulable from a first position spaced from the housing to a second position spaced closer to the housing than the first position to cause the piston to move in a proximal direction as the piston moves along the longitudinal bore in the inserter head with the piston distal end moving from a first piston position spaced from the inserter head to a second piston position closer to the inserter head than the first piston position, and e) wherein with the piston in the first piston position, the piston ferrule is unthreadable from its wedging relationship with the distal end of the drive train to enable the piston to be separable from the drive train such that the distal end of the drive train is then configured for threadingly engaging a second piston with a second ferrule that is configured to be threadable into a wedging relationship with the drive train.

\* \* \* \* \*

UNITED STATES PATENT AND TRADEMARK OFFICE
CERTIFICATE OF CORRECTION

| | | |
|---|---|---|
| PATENT NO. | : 8,236,004 B2 | Page 1 of 1 |
| APPLICATION NO. | : 12/685019 | |
| DATED | : August 7, 2012 | |
| INVENTOR(S) | : Jonas Burgi | |

It is certified that error appears in the above-identified patent and that said Letters Patent is hereby corrected as shown below:

On the title page of Patent 8,236,004, (75) Inventor: "Burgi Jonas" should be "Jonas Burgi".

Signed and Sealed this
Second Day of October, 2012

David J. Kappos
*Director of the United States Patent and Trademark Office*